United States Patent
Gudas et al.

(10) Patent No.: US 10,265,378 B2
(45) Date of Patent: Apr. 23, 2019

(54) COMBINATION THERAPY FOR HEAD AND NECK CANCER

(71) Applicant: Cornell University, Ithaca, NY (US)

(72) Inventors: Lorraine J Gudas, New York, NY (US); Xiao-Han Tang, Staten Island, NY (US); Kwame Osei-Sarfo, Astoria, NY (US); Alison Urvalek, Astoria, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/125,081

(22) PCT Filed: Mar. 9, 2015

(86) PCT No.: PCT/US2015/019528
§ 371 (c)(1),
(2) Date: Sep. 9, 2016

(87) PCT Pub. No.: WO2015/138354
PCT Pub. Date: Sep. 17, 2015

(65) Prior Publication Data
US 2017/0072010 A1 Mar. 16, 2017

Related U.S. Application Data

(60) Provisional application No. 61/950,480, filed on Mar. 10, 2014.

(51) Int. Cl.
| | | |
|---|---|---|
| A61K 31/192 | (2006.01) | |
| A61K 38/17 | (2006.01) | |
| A61K 45/06 | (2006.01) | |
| A61K 31/203 | (2006.01) | |
| A61K 31/44 | (2006.01) | |
| A61K 9/00 | (2006.01) | |

(52) U.S. Cl.
CPC .......... *A61K 38/177* (2013.01); *A61K 9/0019* (2013.01); *A61K 9/0053* (2013.01); *A61K 31/192* (2013.01); *A61K 31/203* (2013.01); *A61K 31/44* (2013.01); *A61K 45/06* (2013.01)

(58) Field of Classification Search
CPC .................................................. A61K 31/192
See application file for complete search history.

(56) References Cited

U.S. PATENT DOCUMENTS

2012/0094956 A1  4/2012  Chandraratna

FOREIGN PATENT DOCUMENTS

| WO | WO 2011/103321 | 8/2011 |
| WO | WO 2012/178108 | 12/2016 |

OTHER PUBLICATIONS

International Search Report dated Jul. 15, 2016.
Gudas et al., 1994, The Retinoids: Biology, Chemistry, and Medicine, eds Sporn MB, Roberts AB, & Goodman DS (Raven Press, New York), pp. 443-520 "11 / Cellular Biology and Biochemistry of the Retinoids".
Chambon P, 1996, FASEB J. 10:940-954; Mongan NP & Gudas LJ, 2007, Differentiation 75(9):853-870; Tang XH & Gudas LJ, 2011, Annu Rev Pathol 6:345-364 "A decade of molecular biology of retinoic acid receptors".
Pérez E, Bourguet W. Gronemeyer H, & de Lera AR, 2012, Biochim Biophys Acta 1821(1):57-69. "Modulation of RXR Function Through Ligand Design".
Connolly RM, Nguyen NK, & Sukumar S, 2013, Clin Cancer Res 19(7):1651-1659; "Molecular Pathways: Current Role and Future Directions of the Retinoic Acid Pathway in Cancer Prevention and Treatment".
Dragnev KH, et al., 2007, Clin Cancer Res 13(6):1794-1800; "A Proof-of-Principle Clinical Trial of Bexarotene in Patients With Non-Small Cell Lung Cancer".
Dragnev KH, et al., 2011, Cancer Prev Res (Phila) 4(6):818-828 "Bexarotene Plus Erlotinib Suppress Lung Carcinogenesis Independent of KRAS Mutations in Two Clinical Trials and Transgenic Models".
Shilkaitis A, Bratescu L., Green A, Yamada T, & Christov K, 2013, Cancer Prev Res (Phila) 6(4):299-308, "Bexarotene Induces Cellular Senesce in MMTV-Neu Mouse Model of Mammary Carcinogenesis".
Hatoum A, El-Sabban ME, Khoury J, Yuspa SH, & Darwiche N, 2001, Carcinogenesis 22(12):1955-1963. "Overexpression of Retinoic Acid Receptors Alpha and Gamma Into Neoplastic Epidermal Cells Causes Retinoic Acid-Induced Growth Arrest and Apoptosis".
Lippman SM, Sudbo J, & Hong WK, 2005, J Clin Oncol 23(2):346-356. "Oral Cancer Prevention and the Evolution of Molecular Trageted Drug Development".
Lippman et al. 1993, N Engl J Med. "Comparison of Low-Dose Isoretinoin Beta Carotene to Prevent Oral Carcinogensis" vol. 328 No. 1 15-20.
Gniadecki R, et al., 2007, Br J Dermatol 157(3):433-440. "The Optimal Use of Bexarotene in Cutaneous T-Cell Lymphoma".
Abba MC, et al., 2009, Cancer Prev Res (Phila) 2(2):175-184. "Indentification of Modulated Genes by Three Classes of Chemopreventive Agents at Preneoplastic Stages in a P53-Null Mouse Mammary Tumor Model".
Kim HT, et al., 2006, Cancer Res 66(24):12009-12018. "Identification of Biomarkers Modulated by the Rexinoid Lgd1069 (Bexarotene in Human Breast Cells Using Oligonucleotide Arrays".
Office Action for corresponding CN application No. 201580024532. 1dated Sep. 4, 2018.
Idres N. et al, "Regulation of CYP26A1 expression by selective RAR and RXR agonists in human NB4 promyelocytic leukemia cells", Biochemical Pharmacolog, vol. 69, No. 11, pp. 1595-1601, published on Jun. 30, 2005.
Supplementary European Search Report for corresponding EP application 15761565.9 dated Aug. 21, 2017.

*Primary Examiner* — Samira J Jean-Louis
(74) *Attorney, Agent, or Firm* — Mark S. Cohen; Pearl Cohen Zedek Latzer Baratz LLP

(57) ABSTRACT

This invention relates to pharmaceutical composition and methods of using RXR agonist and/or RAR agonist for the treatment or prevention of head and neck cancer.

10 Claims, 11 Drawing Sheets
Specification includes a Sequence Listing.

4-HNE

β-catenin

MMP9

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 1
ccgtcgtaac ctgttgagta actat                                          25

<210> SEQ ID NO 2
<211> LENGTH: 26
<212> TYPE: DNA
<213> ORGANISM: Artificial Sequence
<220> FEATURE:
<223> OTHER INFORMATION: Synthetic oligonucleotide sequence

<400> SEQUENCE: 2 gtctacccatt atacaccaca ccgtaa                                         26

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide sequence

<400> SEQUENCE: 3
acttcctccg tagagcatc                                                  19

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide sequence

<400> SEQUENCE: 4
gcagagttgg tgtccattc                                                  19

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide sequence

<400> SEQUENCE: 5
agaacaaccc agctctggag aaa                                             23

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide sequence

<400> SEQUENCE: 6
acaccctcca gaaagcgaga gt                                              22
```

COMBINATION THERAPY FOR HEAD AND NECK CANCER

CROSS-REFERENCE TO RELATED APPLICATIONS

This application is a National Phase Application of PCT International Application PCT/US15/19528, filed Mar. 9, 2015, which claims priority to U.S. Provisional Application No. 61/950,480, filed on Mar. 10, 2014, all of which are incorporated by reference herein in their entirety

GOVERNMENT FUNDING

This invention was made with Government support by National Institutes of Health (NIDCR) Grant Number R01 10389, NIH postdoctoral fellowship NIAAA F32-AA021045, and NIH Grant Number R01AA018332. The United States Government has certain rights in the invention.

FIELD OF THE INVENTION

The invention relates to the treatment and prevention of head and neck cancer.

BACKGROUND OF THE INVENTION

Retinoids, including vitamin A (retinol) and its metabolites such as all-trans retinoic acid (RA), regulate cell proliferation and differentiation (Gudas et al., 1994, *The Retinoids: Biology, Chemistry, and Medicine*, eds Sporn M B, Roberts A B, & Goodman D S (Raven Press, New York), pp 443-520). RA regulates gene expression by binding and activating retinoic acid receptors (RARs α, β, and γ) and retinoid X receptors (RXRs α, β, and γ), transcription factors that heterodimerize and associate with retinoic acid response elements (RAREs) (Chambon P, 1996, *FASEB J.* 10:940-954; Mongan N P & Gudas L J, 2007, *Differentiation* 75(9):853-870; Tang X H & Gudas L J, 2011, *Annu Rev Pathol* 6:345-364.)

Retinoid X receptors (RXRs) play a key role within the nuclear receptor (NR) superfamily and can form heterodimers with many other nuclear receptors, including RARs, PPARs, liver X receptors (LXR), farnesoid X receptor (FXR) (Perez E, Bourguet W, Gronemeyer H, & de Lera A R, 2012, *Biochim Biophys Acta* 1821(1):57-69.), and vitamin D receptor (VDR) (Perez E, Bourguet W, Gronemeyer H, & de Lera A R, 2012, *Biochim Biophys Acta* 1821(1): 57-69; Germain P, et al. 2006, *Pharmacol Rev* 58(4):760-772.). Because RXRs participate in many nuclear receptor signaling pathways, they have been a target for drug discovery (Perez E, Bourguet W, Gronemeyer H, & de Lera A R, 2012, *Biochim Biophys Acta* 1821(1):57-69.).

The retinoic acid receptor (RAR) is a type of nuclear receptor that is activated by both all-trans retinoic acid and 9-cis retinoic acid. The effects of RA on cells and tissues are known to occur through the activation of retinoic acid receptors (RARα, RARβ, and RARγ) and their isoforms (Chambon P, 1996, *FASEB J.* 10:940-954; Tang X H & Gudas L J, 2011, *Annu Rev Pathol* 6:345-364).

Head and neck cancer is a group of cancers that start in the lip, oral cavity (mouth), nasal cavity (inside the nose), paranasal sinuses, pharynx, and larynx. These cancers are biologically similar, with 90% of head and neck cancers are squamous cell carcinomas originating from the mucosal lining (epithelium) of these regions. These cancers are frequently aggressive in their biologic behavior, and patients with these types of cancer are at a higher risk of developing another cancer in the head and neck area.

Natural and synthetic retinoids have shown efficacy in the prevention and treatment of human cancers including leukemia, breast and lung cancers (Connolly R M, Nguyen N K, & Sukumar S, 2013, *Clin Cancer Res* 19(7):1651-1659; Dragnev K H, et al., 2007, *Clin Cancer Res* 13(6):1794-1800; Dragnev K H, et al., 2011, Cancer Prev Res (Phila) 4(6):818-828; Gniadecki R, et al., 2007, Br J Dermatol 157(3):433-440.). Bexarotene inhibits cell proliferation and induces cellular senescence and apoptosis in a mouse breast cancer model (Shilkaitis A, Bratescu L, Green A, Yamada T, & Christov K, 2013, *Cancer Prev Res (Phila)* 6(4):299-308.), and modulates expression of genes related to the cell cycle, cell differentiation/apoptosis, and cell adhesion/migration in a mouse breast cancer model (Abba M C, et al., 2009, *Cancer Prev Res (Phila)* 2(2):175-184.) and in human normal mammary epithelial cells (Kim H T, et al., 2006, *Cancer Res* 66(24):12009-12018.). RARγ also mediates RA-induced growth arrest and apoptosis of neoplastic mouse papilloma cell lines (Hatoum A, El-Sabban M E, Khoury J, Yuspa S H, & Darwiche N, 2001, *Carcinogenesis* 22(12):1955-1963.).

Head and neck cancer is often treated with some form of surgery, with the goal of removing the cancerous cells entirely. This can be particularly difficult if the cancer is near the larynx and can result in the patient being unable to speak. Surgery is also commonly used to remove some or all of the cervical lymph nodes to prevent further spread of the disease. Radiation therapy may also play an important role. Treatment with 13-cis RA, which can be isomerized to RA, a pan-RAR agonist, resulted in reductions in the sizes of oral leukoplakias in patients (Connolly R M, Nguyen N K, & Sukumar S, 2013, *Clin Cancer Res* 19(7):1651-1659; Lippman S M, et al., 1993, *N Engl J Med* 328(1):15-20.). The effectiveness of radiation and chemotherapy, however, is often limited; while side effects may be significant.

Head and neck cancer is strongly associated with certain environmental and lifestyle risk factors, including tobacco smoking, alcohol consumption, UV light, particular chemicals used in certain workplaces, and certain strains of viruses, such as human papillomavirus (HPV) and Epstein-Barr virus (EBV). Cigar smoking is an important risk factor for oral cancers as well. Head and neck cancers, however, are often not diagnosed early enough for the most effective treatment. For example, about 60-70% of oral cavity carcinoma cases are diagnosed only after the tumors have become locally advanced (Lippman S M, Sudbo J, & Hong W K, 2005, *J Clin Oncol* 23(2):346-356.). Therefore, there is a need for alternative treatments that prevent or slow the progression of head and neck cancer using novel pharmaceutical compositions.

SUMMARY OF THE INVENTION

This invention discloses pharmaceutical compositions and methods for treating and preventing head and neck cancer.

According to certain embodiments, the invention provides a pharmaceutical composition comprising a RXR agonist and a RAR agonist.

In certain embodiments, the amount of the RXR agonist or RAR agonist is from 50 mg to about 500 mg.

In certain embodiments, the concentration of the RXR agonist or RAR agonist is from about 1 mg to about 10 mg per 100 ml.

The RXR agonist may be a highly specific RXR agonist according to certain embodiments.

In certain embodiments, the RXR agonist is bexarotene.

The RAR agonist may be a highly specific RAR agonist according to certain embodiments.

In certain embodiments, the RAR agonist is a RARγ agonist.

In certain embodiments, the RARγ agonist is CD1530.

According to certain embodiments, the invention provides a method of treating or preventing head and neck cancer in a subject comprising administering to the subject a RXR agonist and/or a RAR agonist.

The head and neck cancer is oral cancer according to certain embodiments.

In certain embodiments, the head and neck cancer is oral cavity squamous cell carcinoma.

In certain embodiments, the head and neck cancer is esophageal squamous cell carcinoma.

In certain embodiments, the head and neck cancer is malignant squamous cell carcinomas The head and neck cancer is caused by tobacco or cigar smoking according to certain embodiments.

The head and neck cancer is caused by alcohol according to certain embodiments.

The head and neck cancer is caused by virus according to certain embodiments.

In certain embodiments, the virus is human papillomavirus (HPV).

In certain embodiments, the virus is Epstein-Barr virus (EBV).

The head and neck cancer is caused by exposure to a carcinogen according to certain embodiments.

In certain embodiments, the head and neck cancer is caused by exposure to irradiation.

The head and neck cancer may have become locally advanced according to certain embodiments.

According to certain embodiments, the invention provides a method of treating or preventing head and neck cancer in a subject comprising administering to the subject a RXR agonist and/or a RAR agonist.

According to certain embodiments, the invention provides a method of reducing cell proliferation or cell cycle progression in a subject comprising administering to the subject a RXR agonist and/or a RAR agonist.

According to certain embodiments, the invention provides a method of reducing the level of β-catenin in a subject comprising administering to the subject a RXR agonist and/or a RAR agonist.

According to certain embodiments, the invention provides a method of reducing the level of MMP9 protein in a subject comprising administering to the subject a RXR agonist and/or a RAR agonist.

According to certain embodiments, the invention provides a method of reducing the level of reactive oxygen species (ROS) in a subject comprising administering to the subject a RXR agonist and/or a RAR agonist.

According to certain embodiments, the invention provides a method of reducing the number of cancer stem cells in the oral cavity in a subject comprising administering to the subject a RXR agonist and/or a RAR agonist.

According to certain embodiments, the invention provides a method of reducing tongue tumor development in a subject comprising administering to the subject a RXR agonist and/or a RAR agonist.

According to certain embodiments, the invention provides a method of reducing cell cycle gene progression in a subject comprising administering to the subject a RXR agonist and/or a RAR agonist.

In certain embodiments, the gene involved in cell cycle progression is selected from the group consisting of: aurora kinase A, aurora kinase B, CDK1, CDK6, cyclin A2, cyclin B1, and cyclin E1.

According to certain embodiments, the invention provides a method of reducing DNA replication gene ontology in a subject comprising administering to the subject a RXR agonist and/or a RAR agonist.

In certain embodiments, the gene involved in DNA replication is selected from the group consisting of: minichromosome maintenance (MCM) complex members 2-7 and 10, DNA replication helicase 2 (DNA2), DNA ligase 1 (LIG1), origin recognition complex subunit 1 (ORC1), DNA polymerase alpha 1 (POLA1), the catalytic subunit of DNA polymerase, and DNA primase large subunit (PRIM2).

According to certain embodiments, the invention provides a method of reducing cell migration gene ontology in a subject comprising administering to said subject a RXR agonist and/or a RAR agonist.

In certain embodiments, the gene involved in cell migration is selected from the group consisting of: Matrix metalloproteinases MMP3, MMP9, MMP10, MMP12, MMP13, MMP14, and tenascin C (TNC).

According to certain embodiments, the invention provides a method of reducing mitosis gene expression in a subject comprising administering to the subject a RXR agonist and/or a RAR agonist.

According to certain embodiments, the invention provides a method of reducing TCA cycle and oxidative phosphorylation gene expression in a subject comprising administering to the subject a RXR agonist and/or a RAR agonist.

In certain embodiments, the gene involved in TCA cycle and oxidative phosphorylation is selected from the group consisting of: hypoxia-inducible factor 1α (HIF1α), glucose transporter 1 (GLUT1), monocarboxylate transporter 4 (Slc16a3, MCT4), and NADH dehydrogenase (ubiquinone) 1 alpha subcomplex 4-like (Ndufa4l2).

According to certain embodiments, the invention provides a method of maintaining or restoring transcription profile in a subject comprising administering to the subject a RXR agonist and/or a RAR agonist.

According to certain embodiments, the invention provides a method of reducing cancerous lesion severity in a subject comprising administering to the subject a RXR agonist and/or a RAR agonist.

According to certain embodiments, the invention provides a method of reducing the number of cancerous lesions in a subject comprising administering to the subject a RXR agonist and/or a RAR agonist.

In certain embodiments, the lesion is neoplastic tongue lesion.

According to certain embodiments, the invention provides a method of reducing hyperplasia in a subject comprising administering to the subject a RXR agonist and/or a RAR agonist.

According to certain embodiments, the invention provides a method of reducing malignant squamous cell carcinomas in a subject comprising administering to the subject a RXR agonist and/or a RAR agonist.

In certain embodiments, the RXR agonist and/or a RAR agonist is administered three times daily.

In certain embodiments, the RXR agonist and/or a RAR agonist is administered daily for at least seven consecutive days.

In certain embodiments, the RXR agonist and/or a RAR agonist is administered at an amount from about 5.0 mg to about 500 mg per day.

In certain embodiments, the RXR agonist and/or a RAR agonist is administered orally.

The RXR agonist and/or a RAR agonist may be administered in drinking water or in an oral rinse according to certain embodiments.

In certain embodiments, the RXR agonist and/or a RAR agonist is administered intravenously or subcutaneously.

The RXR agonist and/or a RAR agonist do not elevate serum triglyceride in the subject according to certain embodiments.

The RXR agonist and/or a RAR agonist do not increase cardiovascular risk in the subject according to certain embodiments.

In certain embodiments, a therapeutic effective amount of the RXR agonist and/or a RAR agonist is administered.

The RXR agonist administered is a highly specific RXR agonist according to certain embodiments.

The RXR agonist administered is bexarotene according to certain embodiments.

The RAR agonist administered is a highly specific RAR agonist according to certain embodiments.

The RAR agonist administered is a RARγ agonist according to certain embodiments.

The RARγ agonist administered is CD1530 according to certain embodiments.

DETAILED DESCRIPTION OF THE INVENTION

Figure 1A:
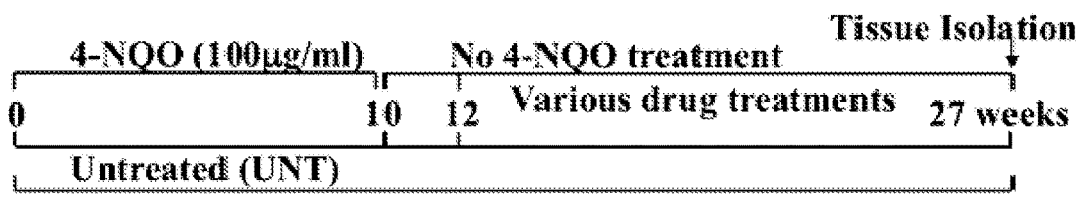
FIG. 1. The combination of bexarotene and CD1530 reduced average gross cancerous lesion numbers and lesion grades in mouse tongues. A. Brief diagram of the experimental protocol (see MATERIALS AND METHODS). B. Representative gross morphology of the mouse tongues from groups in this study and the gross tongue lesion grading system (8×), severity 4>3>2>1>0. C. Representative histology of pathological stages of tongue lesions: a, normal (untreated tongue); b, hyperplasia; c, dysplasia; d, papilloma; e, invasive squamous cell carcinoma. D. Number of cancerous tongue lesions (number of lesions per tongue) as a function of treatment. E. Severity of tongue lesions as a function of treatment. In D & E, a one way analysis of variance test was used to analyze the differences in the tongue lesion numbers and severity among all treatment groups (UNT, n=15; 4-NQO, n=10; 4N+B, n=12; 4N+C, n=13; 4N+B+C, n=10). Differences with p values of <0.05 between the 4-NQO and the 4N+B, 4N+C, 4N+B+C groups were considered statistically significant (*, $p<0.05$; , $p<0.01$; *, $p<0.001$). UNT, untreated; 4-NQO, 4-NQO treatment; 4N+B, 4-NQO+bexarotene; 4N+C, 4-NQO+CD1530; 4N+B+C, 4-NQO+bexarotene+CD1530.
Figure 1B:
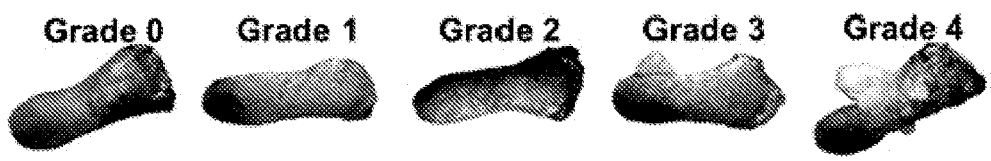
Figure 1C:
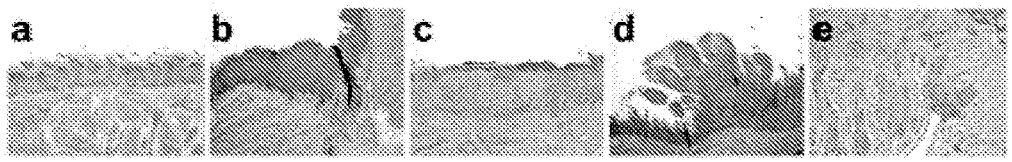

As discussed above, there remains a need to provide alternate treatment and prevention of head and neck cancer using novel pharmaceutical compositions. Accordingly, the present invention relates to pharmaceutically compositions comprising an RXR agonist and/or RAR agonist, and uses thereof in this regard.

As used herein, the terms "cancer", "tumor" and "cell proliferative disorder" are used interchangeably to refer to a cellular disorder characterized by uncontrolled or disregulated cell proliferation, decreased cellular differentiation, inappropriate ability to invade surrounding tissue, and/or ability to establish new growth at ectopic sites. The terms further encompass primary and metastatic cancers.

Head and neck cancer is a group of cancers that start in the lip, oral cavity (mouth), nasal cavity (inside the nose), paranasal sinuses, pharynx, and larynx. Oral cavity squamous cell carcinoma (OCSCC), a head and neck cancer, is one of the most common human cancers in the world (Siegel R, Naishadham D, & Jemal A, 2013, *CA Cancer J Clin* 63(1):11-30.). The two major etiological factors in OCSCC are tobacco and alcohol (Binnie W H, Rankin K V, & Mackenzie I C, 1983, *J Oral Pathol* 12(1):11-29; Lippman S M, Sudbo J, & Hong W K, 2005, *J Clin Oncol* 23(2):346-356.). Oral cavity squamous cell carcinoma (SCC) development is a complicated, multi-step process that involves genetic, epigenetic, and metabolic changes (Haddad R I & Shin D M, 2008, *N Engl J Med* 359(11):1143-1154.). Other types of head and neck cancer include, but are not limited to, nasopharynx cancer (nasopharynx), oropharyngeal cancer, hypopharynx, laryngeal cancer (larynx), trachea and others. Environmental and lifestyle risk factors for head and neck cancer include, but are not limited to, tobacco smoking, cigar smoking, alcohol consumption, UV light, particular chemicals used in certain workplaces, and certain strains of viruses, such as human papillomavirus (HPV) and Epstein-Barr virus (EBV).

The retinoid X receptor (RXR) are encoded by three distinct human genes, RXRα, RXRβ, and RXRγ (Germain et al., (2006) International Union of Pharmacology. LXIII. Retinoid X receptors. Pharmacol. Rev., 58 (4): 760-72). RARs and RXRs belong to two different groups of the nuclear receptor superfamily, suggesting different functions. RXRs are expressed primarily in visceral organs such as the liver and kidney. Activated RXRs form homodimers or heterodimers with retinoic acid receptors, vitamin D receptors, thyroid receptors or peroxisome proliferator-activated receptors. Once activated, these retinoid receptor dimers bind to DNA at retinoic acid response elements and act as transcription factors that regulate the expression of genes which control cellular differentiation and proliferation. Retinoid agonists can activate the expression of retinoid regulated genes by removing negative transcription control or by facilitating positive transcriptional activity.

There are also three retinoic acid receptors (RAR), RARα, RARβ, and RARγ, encoded by the RARα, RARβ, RARγ genes, respectively. Each receptor isoform has several splice variants: two—for α, four—for β, and two—for γ. RAR heterodimerizes with RXR and in the absence of ligand, the RAR/RXR dimer binds to hormone response elements known as retinoic acid response elements (RAREs) in a complex with corepressor protein. Binding of agonist ligands to RAR results in dissociation of corepressor and recruitment of coactivator protein that, in turn, promotes transcription of the downstream target gene into mRNA and eventually protein.

The term "agonist" according to the present invention refers to an agonist of an RXR (RXRα, RXRβ, and/or RXRγ), or RAR (RXRα, RXRβ, and/or RXRγ).

Known RXR agonists include but are not limited to: bexarotene, AGN194204, LG100268, 9-cis-retinoic acid, methoprene acid, and SR11237.

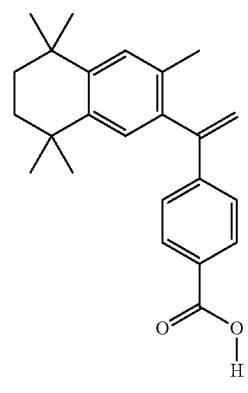

Bexarotene

-continued
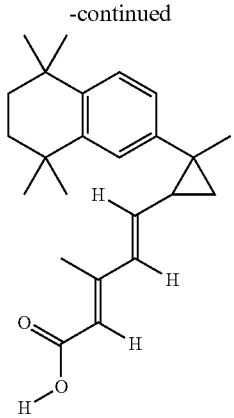
AGN194204
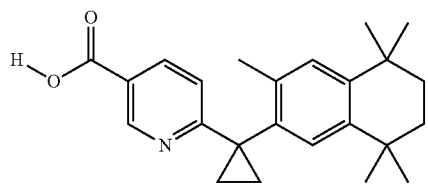
LG100268
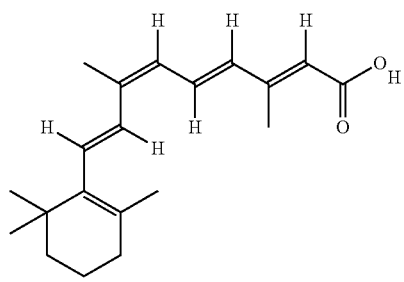
9-cis-retinoic acid
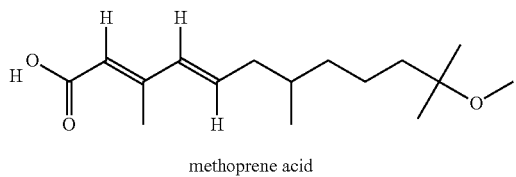
methoprene acid
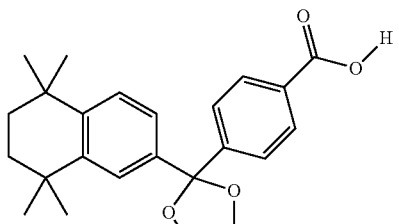
SR11237
Known RARα agonists include but are not limited to: TTNPB, tamibarotene, 9-cis-retinoic acid, all-trans-retinoic acid, AGN193836, Ro 40-6055, CD666, and BMS753.
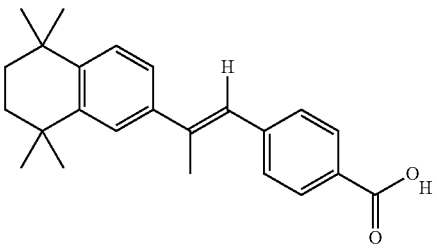
TTNPB
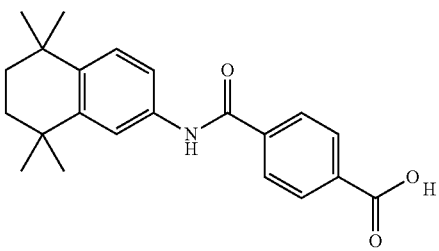
Tamibarotene
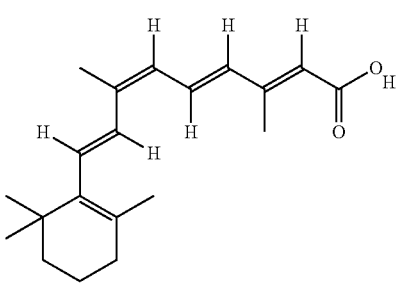
9-cis-retinoic acid
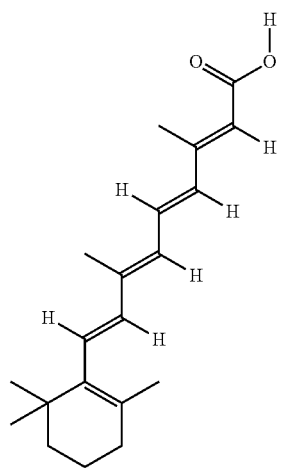
all-trans-retinoic acid

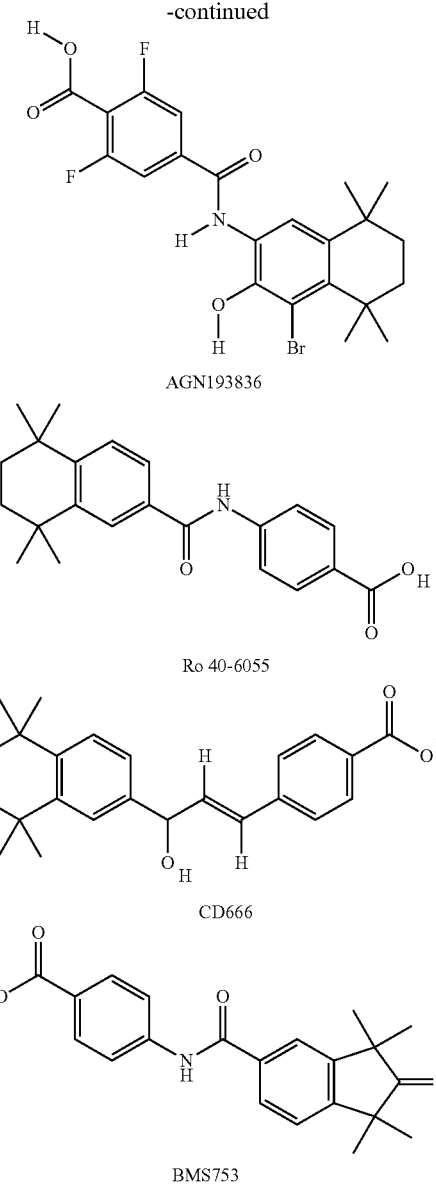

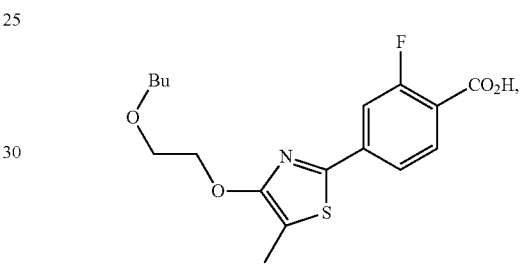

The term "highly-specific RAR agonist" refers to an RAR agonist that has the highest affinity for agonists of a particular isoform selected from the group consisting of RARα, RARβ, and RARγ. The term also includes other agonists of that particular isoform having a binding affinity similar to the agonist having the highest affinity, e.g., at least 50% or greater, preferably 75% or greater, more preferably 90% or greater of the highest binding affinity.

The term "highly-specific RXR agonist" refers to an RXR agonist that has the highest affinity for agonists of a particular isoform selected from the group consisting of RXRα, RXRβ, and RXRγ. The term also includes other agonists of that particular isoform having a binding affinity similar to the agonist having the highest affinity, e.g., at least 50% or greater, preferably 75% or greater, more preferably 90% or greater of the highest binding affinity.

Known RARβ agonists include but are not limited to: AC261066, AC55649, LE135, Tazarotene, Adapalene, CD666, 9-cis-retinoic acid, BMS641 and TTNPB. AC261066 and AC55649 are highly-specific RARβ ago-nists. The term "highly-specific RARβ agonist" also includes other agonists having a binding affinity similar to AC261066 or AC55649, e.g., at least 50% or greater, preferably 75% or greater, more preferably 90% or greater of the RARβ binding affinity of AC261066 or AC55649. The term "highly-specific RARγ agonist" refers to CD1530, and also include other agonists having a binding affinity similar to CD1530, e.g., at least 50% or greater, preferably 75% or greater, more preferably 90% or greater of the RARγ binding affinity of CD1530. The term "highly-specific RARα agonist" refers to AM580, and also include other agonists having a binding affinity similar to AM580, e.g., at least 50% or greater, preferably 75% or greater, more preferably 90% or greater of the RARα binding affinity of AM580.

RARβ agonists include the fluorinated alkoxythiazoles previously described (65), such as:

4'-Octyl-[1,1'-biphenyl]-4-carboxylic acid (65), Adapalene (67), BMS-231973, BMS-228987, BMS-276393, BMS-209641 (66), BMS-189453 {4-[(1E)-2-(5,6-Dihydro-5,5-dimethyl-8-phenyl-2-naphthalenyl)ethenyl]-benzoic acid} (68), CD2019 (6-[4-methoxy-3-(1-methylcyclohexyl)phenyl]naphthalene-2-carboxylic acid), compounds described in WO2008/064136 and WO2007009083 and tazarotene (ethyl 6-[2-(4,4-dimethyl-3,4-dihydro-2H-1-benzothiopyran-6-yl)ethynyl] pyridine-3-carboxylate).

AC261066:

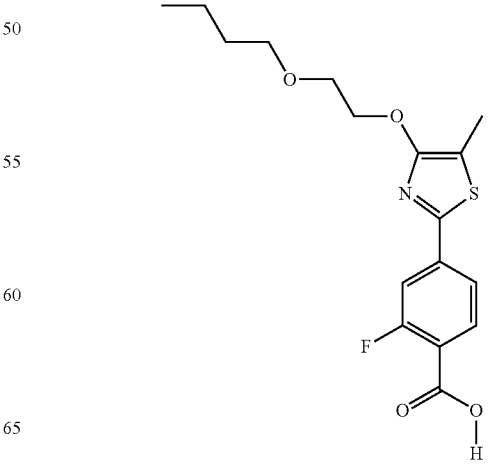

AC55649:
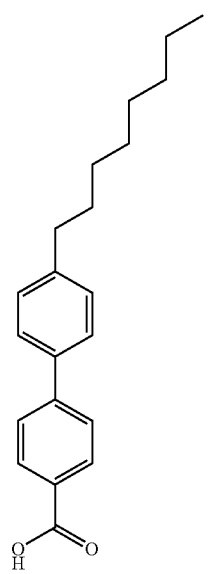
Tazarotene:
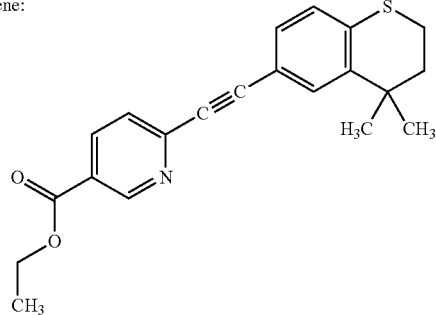
Adapalene:
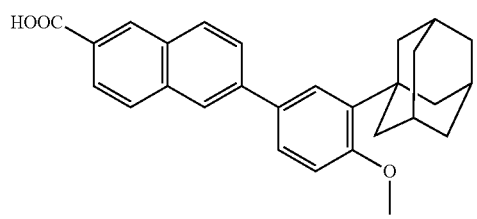
CD666:
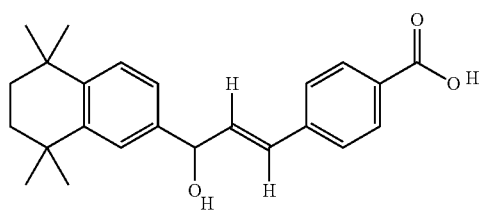
9-cis-retinoic acid:
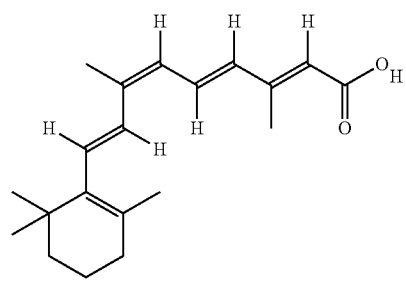
BMS641:
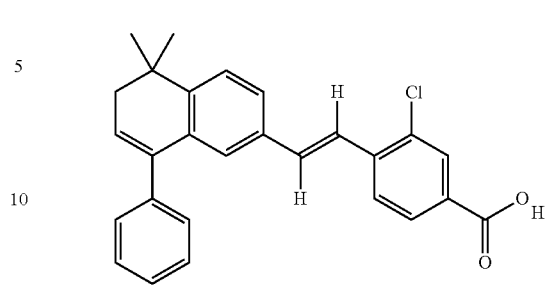
TTNPB:
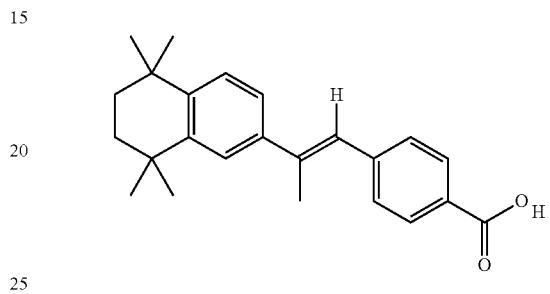
Known RARγ agonists include but are not limited to: CD1530, TTNPB, BMS270394, all-trans-retinoic acid, 9-cis-retinoic acid, CD666, and AHPN.
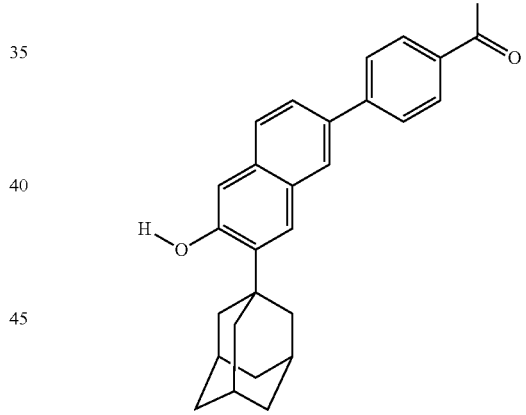
CD1530
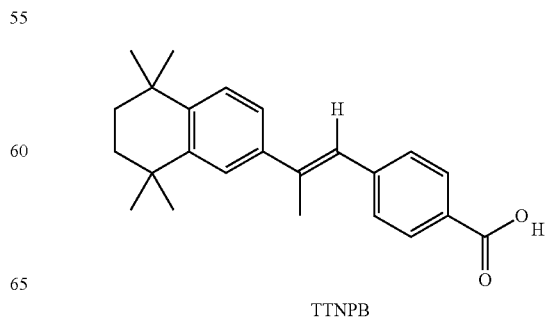
TTNPB -continued

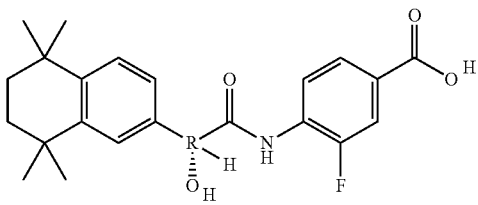

BMS270394

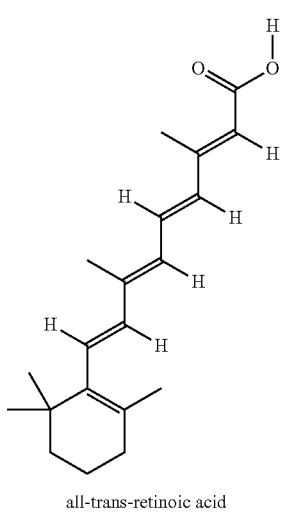

all-trans-retinoic acid

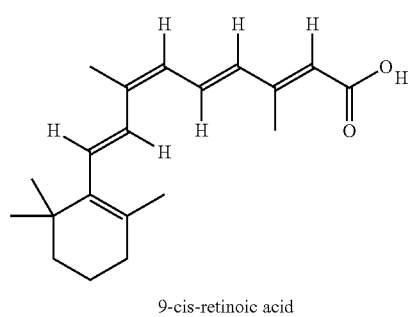

9-cis-retinoic acid

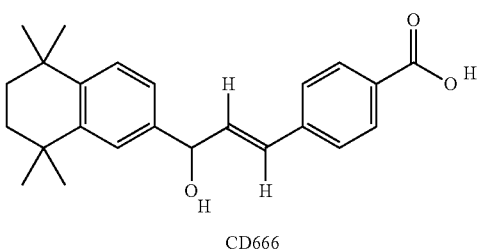

CD666

-continued

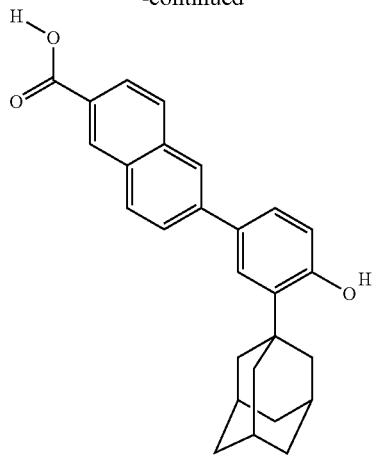

AHPN

The inventors of the present application induced oral cavity SCCs that mimic human oral tumors in terms of their morphological, histopathological, and molecular characteristics in mice by adding the carcinogen 4-nitroquinoline 1-oxide (4-NQO) to the drinking water (Tang X H, Albert M, Scognamiglio T, & Gudas L J, 2009, Cancer Prev Res (Phila Pa.) 2(12):1100-1110; Tang X H, Knudsen B, Bemis D, Tickoo S, & Gudas L J, 2004, Clin Cancer Res 10(1 Pt 1):301-313; Vitale-Cross L, et al., 2009, Cancer Prev Res (Phila Pa.) 2(5):419-422.). Therefore, this murine 4-NQO model is an excellent one for the evaluation of potential cancer preventive and therapeutic approaches. Bexarotene, a synthetic, pan-retinoid X receptor (RXR) agonist (Boehm M F, et al., 1995, J Med Chem 38(16):3146-3155.), has shown efficacy in the treatment of human T-cell lymphoma and lung cancer, and was well tolerated by patients (Dragnev K H, et al., 2007, Clin Cancer Res 13(6):1794-1800; Dragnev K H, et al., 2011, Cancer Prev Res (Phila) 4(6):818-828; Gniadecki R, et al., 2007, Br J Dermatol 157(3):433-440.). RARγ has also shown tumor growth suppression in mouse epidermal keratinocytes (Chen C F, Goyette P, & Lohnes D, 2004, Oncogene 23(31):5350-5359.).

Using the animal model developed, the present inventors have examined RXR agonist (e.g., bexarotene), RAR agonist (e.g., CD1530, a synthetic, specific RARγ agonist, see (Chen C F, Goyette P, & Lohnes D, 2004, Oncogene 23(31):5350-5359.), or the combination of a RXR agonist with a RAR agonist for the treatment and prevention of head and neck cancer, e.g., oral cavity carcinogenesis. The inventors discovered that RXR agonist (e.g., bexarotene) alone or RAR agonist (e.g., CD1530) alone has certain effects. Surprisingly, the inventors discovered that for the prevention of murine oral carcinogenesis the combination of bexarotene and CD1530 is more efficacious than bexarotene alone or CD1530 alone (FIG. 1 D, E). The combination of bexarotene and CD1530 is also more effective than either drug alone in preventing the 4-NQO-induced changes in the transcript levels of genes important for tumor development (FIGS. 3 and 4).

Figure 2:
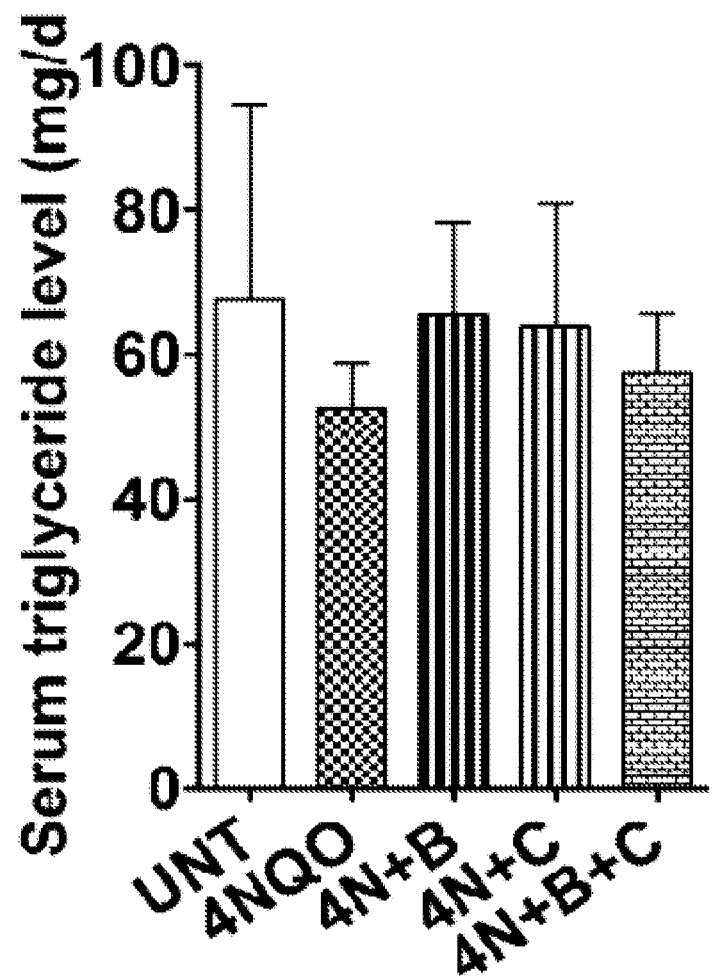
FIG. 2. Mouse serum triglyceride levels following the treatments indicated. UNT (n=4); 4-NQO (n=3); 4N+B (n=4); 4N+C (n=3), and 4N+B+C (n=4). UNT, untreated; 4-NQO, 4-NQO treatment; 4N+B, 4-NQO+bexarotene; 4N+C, 4-NQO+CD1530; 4N+B+C, 4-NQO+bexarotene+CD1530.

The inventors also discovered that bexarotene and/or CD1530, at the dose and the duration used in the present study, did not elevate triglyceride levels (FIG. 2), suggesting that the combination of bexarotene and CD1530 would not cause cardiovascular risks if used at similar doses in cancer prevention treatments for those at risk for oral cancer.

In addition, the inventors discovered that the mRNA levels of several CDKs, cyclins, and proteins involved in DNA replication were lower in the 4N+B group, 4N+C group, and the 4N+B+C group than in the 4-NQO group (FIG. 3).

Figure 5:
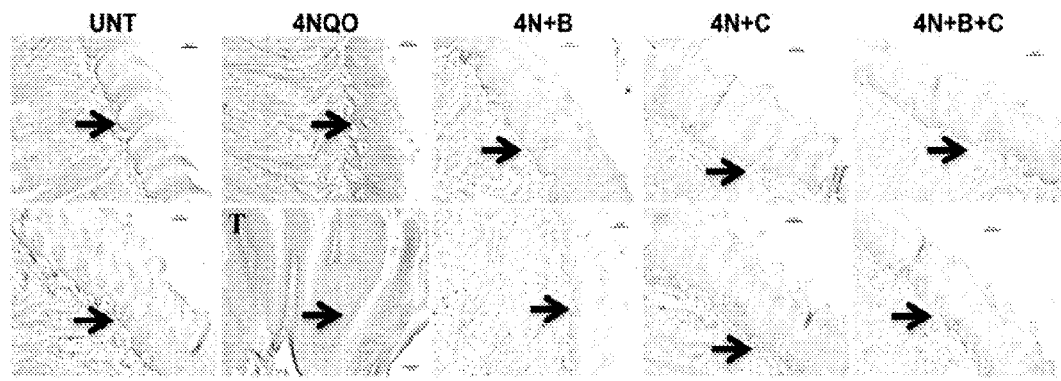
FIG. 5. 4-Hydroxynonenal (4-HNE), an indicator of oxidative stress, in tongue epithelium. The tongues were fixed, embedded in paraffin, and sectioned. Then the tissue sections were stained with an antibody against 4-HNE (magnification, 200×). Four to five representative areas of each tongue section from two mice/group were photographed and analyzed. Two samples/group are shown. UNT, untreated; 4-NQO, 4-NQO treatment; 4N+B, 4-NQO+bexarotene; 4N+C, 4-NQO+CD1530; 4N+B+C, 4-NQO+bexarotene+CD1530. T, tumor. Darker brown indicates more 4-HNE adducts. T, tumor.

Similar to the mechanisms of human oral carcinogenesis (Hanafi R, et al., 2012, Curr Mol Med 12(6):698-703.), one of the mechanisms of 4-NQO induced tumorigenesis is the generation of reactive oxygen species (ROS) that leads to the formation of DNA adducts (Kanojia D & Vaidya M M, 2006, Oral Oncol 42(7):655-667; Nunoshiba T & Demple B, 1993, Cancer Res 53(14):3250-3252.). 4-hydroxynonenal (4-HNE), one of the products generated from excessive ROS, modifies cell proteins by forming protein adducts, and thereby changes cellular signaling cascades and gene expression (Ullery J C & Marnett L J, 2012, Biochim Biophys Acta 1818(10):2424-2435.). The inventors discovered, for the first time, show that both bexarotene, a RXR agonist, and CD1530, a RARγ agonist, suppress excessive ROS production in tongue epithelial cells, and suggest that this inhibition of ROS contributes to the inhibition of tongue carcinogenesis (FIG. 5).

The inventors discovered that the RXR and RARγ agonists in combination reduce the mRNA levels of several MMPs and the protein level of MMP9, suggesting that targeting RXR and RARγ is a useful strategy for the prevention of cancer cell migration and metastasis in other human cancers.

Figure 4A:
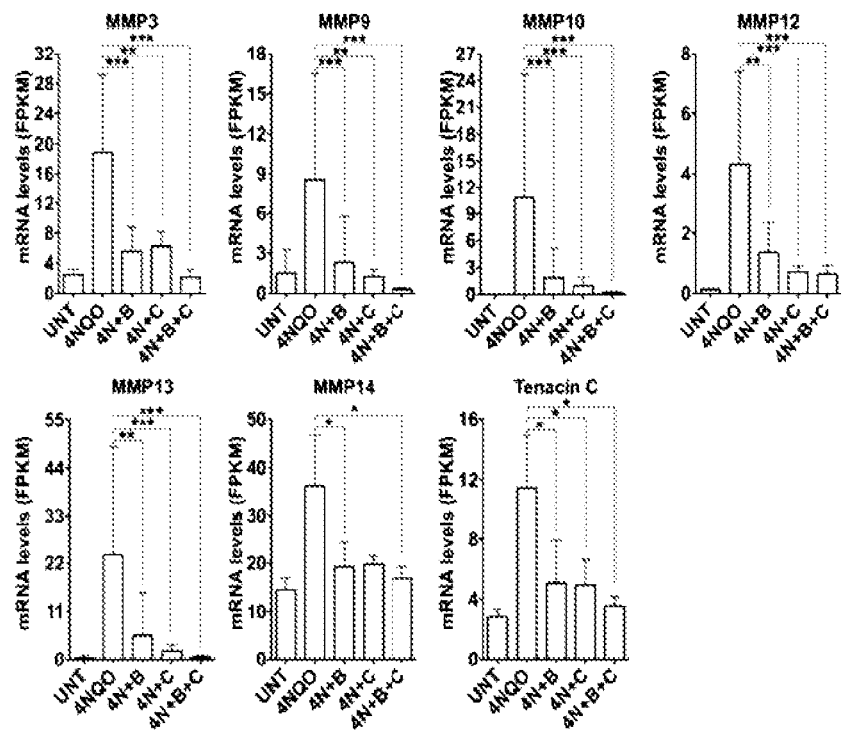
FIG. 4. Quantitative analysis of some transcripts identified from RNA-Seq as involved in extracellular matrix (ECM) breakdown and cell migration, HIF1α signaling, and oral cancer. A. Genes involved in the ECM breakdown and cell migration. B. Genes involved in HIF1α signaling pathway members. C. Genes involved in human oral cancer markers. FPKM, Fragments Per Kilobase of exon model per Million mapped reads; HIF1α, hypoxia-inducible factor 1α; HMMR, hyaluronan-mediated motility receptor; GLUT1, glucose transporter 1; MCT4, monocarboxylate transporter 4; MMP, matrix metalloproteinase; Ndufa4l2, NADH dehydrogenase (ubiquinone) 1 alpha subcomplex, 4-like 2; PTGS2, prostaglandin-endoperoxide synthase 2; TNC, tenascin. Differences with p values of <0.05 between the 4-NQO and the 4N+B, 4N+C, 4N+B+C groups were considered statistically significant (UNT, n=5; 4-NQO, n=3; 4N+B, n=4; 4N+C, n=4; 4N+B+C, n=5; *, $p<0.05$; , $p<0.01$; *, $p<0.001$). UNT, untreated; 4-NQO, 4-NQO treatment; 4N+B, 4-NQO+bexarotene; 4N+C, 4-NQO+CD1530; 4N+B+C, 4-NQO+bexarotene+CD1530.
Figure 4B:
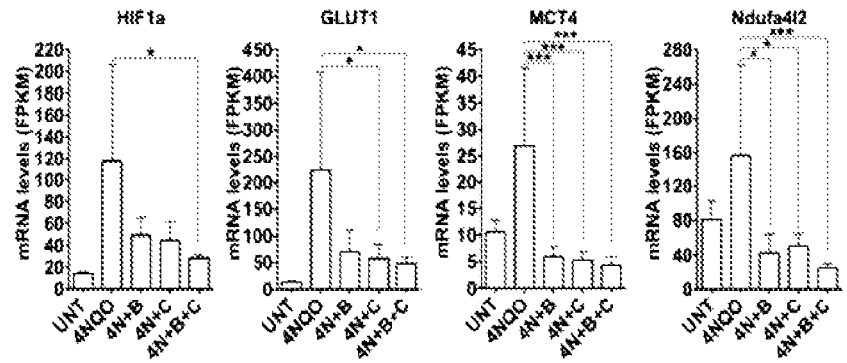

HIF1α regulates genes involved in tumor initiation, progression, and metastasis (Semenza G L, 2012, Cell 148(3): 399-408.), and HIF1α overexpression correlates with a poor prognosis in human head and neck cancer (Eckert A W, et al., 2010, J Oral Pathol Med 39(4):313-317.). The inventors discovered that RARγ and RXR agonists inhibit the HIF1α signaling pathway in the context of tongue carcinogenesis (FIG. 4B). Although the gene ontology and pathway analyses of RNA-Seq data suggest that the TCA cycle and OX-PHOS pathways are significantly less active during tongue carcinogenesis, no significant increases in transcript levels of the glycolysis pathway genes were detected (FIG. 9, Table 1). Therefore, glycolysis is not increased in this 4-NQO model of oral carcinogenesis.

As used herein, the term "subject" means an animal, preferably a mammal, and most preferably a human. A subject may be a patient having a disease or disorder as discussed herein.

As used herein, the term "vitamin A deficiency" refers to a lack of a decreased level of vitamin in serum or an organ (e.g., pancreas, liver, kidney or testes) of an animal, e.g., human.

As used herein, the terms "decrease" and "reduce" are used interchangeably to refer to a negative change in the level, activity or function of a molecule, cell or organ. It is meant that the particular level, activity or function is lower by about 25%, about 50%, about 75%, about 90%, about 1-fold, about 2-fold, about 5 fold, about 10-fold, about 25-fold, about 50-fold, or about 100 fold, or lower, when compared to a control.

As used herein, the terms "increase", "improve", "elevate" and "enhance" are used interchangeably to refer to a positive change in the level, activity or function of a molecule, cell or organ. It is meant that the particular level, activity or function is higher by about 25%, about 50%, about 75%, about 90%, about 1-fold, about 2-fold, about 5 fold, about 10-fold, about 25-fold, about 50-fold, or about 100 fold, or higher, when compared to a control.

The expressions "therapeutically effective" and "therapeutic effect" refer to a benefit including, but not limited to, the treatment or amelioration of symptoms of a proliferative disorder discussed herein. It will be appreciated that the therapeutically effective amount or the amount of agent required to provide a therapeutic effect will vary depending upon the intended application (in vitro or in vivo), or the subject and disease condition being treated (e.g., nature of the severity of the condition to be treated, the particular inhibitor, the route of administration and the age, weight, general health, and response of the individual patient), which can be readily determined by a person of skill in the art. For example, an amount of an agonist is therapeutically effective if it is sufficient to effect the treatment or amelioration of symptoms of a disease discussed herein.

The term "clinically significant level" is used herein to refer to a level of a side effect such as cardiovascular risk caused by the administration of a pharmaceutical composition (e.g., one comprising an agonist) that a physician treating the subject would consider to be significant.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 30%, preferably 20%, more preferably 10%.

As used herein, the term "comprises" means "includes, but is not limited to."

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

If a pharmaceutically acceptable salt of an agonist is utilized in pharmaceutical compositions, the salt preferably is derived from an inorganic or organic acid or base. For reviews of suitable salts, see, e.g., Berge et al, J. Pharm. Sci. 66: 1-19 (1977); Remington: The Science and Practice of Pharmacy, 20th Ed., ed. A. Gennaro, Lippincott Williams & Wilkins, 2000.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The term "carrier" is used interchangeably herein, and includes any and all solvents, diluents, and other liquid vehicles, dispersion or suspension aids, surface active agents, isotonic agents, thickening or emulsifying agents, preservatives, solid binders, lubricants and the like, as suited to the particular dosage form desired. Remington: The Science and Practice of Pharmacy, 20th Ed., ed. A. Gennaro, Lippincott Williams & Wilkins, 2000 discloses various carriers used in formulating pharmaceutically acceptable compositions and known techniques for the preparation thereof.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

The pharmaceutical composition of the present invention can be administered by any method known to one skilled in the art. For example, it may be administered orally or parenterally.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

A composition that comprises the combination of a RXR agonist and a RAR agonist of the present invention, and further with one or more other therapeutic agents can be used, for example, to: 1) enhance the therapeutic effect(s) of the methods of the present invention and/or the one or more other therapeutic agents; 2) reduce the side effects exhibited by the methods of the present invention and/or the one or more other therapeutic agents; and/or 3) reduce the effective dose of an agonist of the present invention and/or the one or more other therapeutic agents.

The amount or suitable dosage of an agonist or a combination of agonists depends upon a number of factors, including the nature of the severity of the condition to be treated, the route of administration and the age, weight, general health, and response of the individual subject. In certain embodiments, the suitable dose level is one that achieves this therapeutic response and also minimizes any side effects associated with the administration. For example, an agonist (either alone or in combination with another agonist) may be administered at an amount from about 30 mg to about 500 mg per day, e.g., about 50 mg to about 500 mg per day, about 100 to about 500 mg per day, about 200 mg to about 500 mg per day, about 100 mg to about 400 mg per day, about 100 mg to about 300 mg per day, about 100 mg to 200 mg per day.

The agonist, alone or in combination with another agonist, may be administered in single or divided or multiple doses. It will be understood that a suitable dosage of an agonist may be taken at any time of the day or night, with food or without food. In some embodiments, the treatment period during which an agent is administered is then followed by a non-treatment period of a particular time duration, during which the therapeutic agents are not administered to the patient. This non-treatment period can then be followed by a series of subsequent treatment and non-treatment periods of the same or different frequencies for the same or different lengths of time.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

EXAMPLES

The present description is further illustrated by the following examples, which should not be construed as limiting in any way. The contents of all cited references (including literature references, issued patents, published patent appli-

Example 1

Materials and Methods

Tumor development in the mouse oral cavity and drug treatments. Six week old wild type C57BL/6 female mice (15 mice/group) were treated with vehicle as a negative control or 100 µg/ml 4-nitroquinoline-1-oxide (4-NQO) for 10 weeks, as previously described (Tang X H, Albert M, Scognamiglio T, & Gudas L J, (2009), Cancer Prev Res (Phila Pa.) 2(12):1100-1110; Tang X H, Knudsen B, Bemis D, Tickoo S, & Gudas L J, 2004, Clin Cancer Res 10(1 Pt 1):301-313.). Two weeks after termination of the carcinogen treatment mice received various drug treatments at doses based on previous studies (Shimono K, et al., 2011, Nat Med 17(4):454-460; Janakiram N B, et al., 2012, Neoplasia 14(2):159-168.): bexarotene at 300 mg/kg in the diet, CD1530 at 2.5 mg/100 ml in drinking water, and the combination of both drugs. The care and use of animals in this study were approved by the Institutional Animal Care and Use Committee (IACUC) of Weill Cornell Medical College.

Tissue dissection, lesion grade measurement, and pathological diagnosis. The tongues of mice were dissected immediately after cervical dislocation. Gross lesions were identified, photographed, counted, and graded (supporting information). The histological diagnosis of squamous neoplasia was performed by a Board-certified pathologist (TS) on paraffin embedded, hematoxylin and eosin (H&E) stained tissue samples in a blinded manner.

RNA-Seq analysis of the mRNA transcriptome. One part of each mouse tongue (same position on each mouse tongue) was snap frozen in liquid $N_2$ and stored at −70° C. until total RNA extraction. Total tissue RNA was extracted and subjected to Next-Generation Sequencing (RNA-Seq) at the Genomics Resources Core Facility, Weill Cornell Medical College. Bioinfomatics analyses were performed using the Tophat and Cufflink software. (supporting information).

Immunohistochemistry. Paraffin embedded tongue sections were stained with various antibodies (supporting information).

Statistical analyses. We performed statistical analyses by one-way analysis of variance and subsequently the Bonferroni test or the Tukey test for multiple comparisons. Differences with a $p<0.05$ (two-tailed test) were considered statistically significant.

Tissue dissection, lesion grade measurement, and pathological diagnosis. The tongues of mice were dissected immediately after cervical dislocation. Gross lesions were identified and photographed, and visible cancerous lesions on the tongues were counted for the examination and multiplicity (i.e., the number of lesions per mouse) with a 8× magnification. The severity of gross lesions on the tongues was quantified by a grading system that included 0 (no lesion), 1 (mild lesion), 2 (intermediate lesion), 3 (severe lesion), and 4 (most severe lesion), respectively, and the average grades from different treatment groups were used for the analyses of the tongue lesions. Mouse tongues were cut longitudinally. One part tissue was fixed in freshly made 4% paraformaldehyde overnight at 4° C., embedded in paraffin, and sectioned into 7-µm sections. One part of each tongue tissue was immediately snap frozen and stored at −70° C. before RNA extraction. The histological diagnosis of squamous neoplasia was performed by a pathologist (T.S.) on the hematoxylin and eosin (H&E) stained, sectioned tissue samples. The lesions observed were classified into three types: epithelial hyperplasia dysplasia (mild, moderate, and severe) and squamous cell carcinoma (SCC), as described previously (Tang X H, Albert M, Scognamiglio T, & Gudas L J, 2009, Cancer Prev Res (Phila Pa.) 2(12):1100-1110; Tang X H, Su D, Albert M, Scognamiglio T, & Gudas L J, 2009, Cancer Biol Ther 8(13):1214-1225.).

Mouse serum triglyceride level measurements. Blood samples from the mice were obtained from mouse tails. The analysis of serum triglyceride levels was carried out at the Laboratory of Comparative Pathology of the Memorial Sloan-Kettering Cancer Center. UNT (n=4); 4-NQO (n=3); 4N+B (n=4); 4N+C (n=3), and 4N+B+C (n=4). UNT, untreated; 4-NQO, 4-NQO treatment; 4N+B, 4-NQO+bexarotene; 4N+C, 4-NQO+CD1530; 4N+B+C, 4-NQO+bexarotene+CD1530.

RNA-Seq analysis of mRNA transcriptome. Representative tongue samples were chosen for the RNA-Seq analysis: untreated (n=5), 4-NQO treatment group (n=3), 4N+B (n=4), 4N+C (n=4), and 4N+B+C (n=5). The extraction of total cellular RNA from mouse tissues was carried out using the RNeasy kit (Qiagen). Subsequent RNA preparation steps were carried out at the Genomics Resources Core Facility of WCMC. The measurement of RNA integrity was determined using the Agilent 2100 BioAnalyzer (Agilent Technologies). Samples with RNA integrity number (RIN) values of 10 were used to construct cDNA libraries. mRNA was purified by using pre-prepared Sera-mag Magnetic Oligo (dT) Beads from Illumina Inc. (SanDiego, Calif.), subjected to thermal fragmentation, and reverse transcribed to first strand cDNA. Following the removal of mRNA strands by RNaseH, first strand cDNAs were used as templates to produce double strand cDNAs, and the overhangs resulting from fragmentation were repaired to blunt ends. An 'A' base was added to the 3' end of cDNAs and subsequently the cDNAs were ligated to Illumina paired end (PE) adaptors that have a single 'T' base overhang at their 3' end. The cDNA-adaptor libraries were purified and enriched by 15 cycles of PCR. The enriched libraries were hybridized to a flow cell and amplified, resulting in ultra-high density flow cells with millions of clusters, each containing about 1,000 copies of the templates. The double stranded cDNA-adaptors were denatured and converted into single strand DNA, and then the template cDNAs were amplified one more time isothermally to produce surface-bound colonies. The clonal DNA clusters were linearized, free 3' OH ends blocked, denatured, hybridized to sequencing primers, and sequenced. The sequencing was conducted by running 4 samples per lane with 51 pair-end cycles on the HISeq2000/1000. The Sequencing-by-Synthesis process used reversible terminators and a DNA polymerase modified to accept reversible terminator nucleotides. After each synthesis cycle the fluorescence of clusters was imaged with high sensitivity. Then the sequencing images were analyzed in three steps, image analysis, base calling, and sequence analysis. The Tophat software was used to align raw sequencing reads against the UCSC mm9 mouse reference genome, and Cufflinks software was employed to measure transcript abundances in the unit of fragments per kilobase of exon model per million mapped reads (FPKM), as well as to perform statistical analysis on the changes in gene expression. The heat maps for genes of interest were generated by R package software. The GEO Accession number is GSE54246; embargoed until publication.

Immunohistochemistry. Paraffin-embedded sections (from two to four mice per group) were deparaffinized and rehydrated, and antigen retrieval was performed using an antigen unmasking solution (Vector Laboratories, H-3300). After quenching endogenous peroxidase with 3% $H_2O_2$, the tissue sections were blocked with the blocking reagent (from the M.O.M. kit from Vector Laboratories for 4-HNE) or 10% goat serum (Vector Laboratories). Then, tissue sections were incubated with a 4-HNE antibody (1:700; mouse monoclonal antibody; Abcam, ab48506), a β-catenin antibody (1:400; rabbit polyclonal antibody; Abcam, ab6302), or a MMP9 antibody (1:70; rabbit polyclonal antibody; Abcam, ab38898), respectively, overnight at 4° C. The sections were then incubated with secondary antibodies (1:200, anti-mouse IgG from the M.O.M kit for 4-1-INE; ready-to-use anti-rabbit IgG from the Invitrogen SuperPicture kit for β-catenin and MMP9). As a negative control, sections were stained without incubation with primary antibodies. The signals were visualized based on a peroxidase detection mechanism with 3,3-diaminobenzidine (DAB) used as the substrate. Four to five representative areas of each mouse tongue section from two to four mice per group were photographed and analyzed.

Real time PCR. Total RNA from mouse tongues was extracted and reverse transcribed to cDNA as described previously (Tang X H, Albert M, Scognamiglio T, & Gudas L J, 2009, Cancer Prev Res (Phila Pa.) 2(12):1100-1110.). Real-time PCR was performed on a MyiQ real-time PCR detection system (Bio-Rad Laboratories) with a SYBR Green Supermix (Quanta). The conditions for the PCR were as follows: 95° C. for 3 min to activate the DNA polymerase, followed by 45 cycles at 94° C. for 30 s, primer annealing at 58° C. for 30 s, and product extension at 72° C. for 30 s. After each cycle, fluorescence was read at 84° C. 36B4 was used as a control (Tang X H, Albert M, Scognamiglio T, & Gudas L J, 2009, Cancer Prev Res (Phila Pa.) 2(12):1100-1110.). The primer sequences were as follows: mouse CDK1, 5'-CCGTCGTAACCTGTTGAGTAACTAT-3' (forward) (SEQ ID NO.: 1) and 5'-GTCTACCCTTATACAC-CACACCGTAA-3' (reverse) (SEQ ID NO.: 2); mouse Cyclin B1, 5'-ACTTCCTCCGTAGAGCATC-3' (forward) (SEQ ID NO.: 3) and 5'-GCAGAGTTGGTGTCCATTC-3' (reverse) (SEQ ID NO.: 4); mouse 36B4, 5'-AGAACAAC-CCAGCTCTGGAGAAA-3' (forward) (SEQ ID NO.: 5) and 5'-ACACCCTCCAGAAAGCGAGAGT-3' (reverse) (SEQ ID NO.: 6). We used the University of California, Santa Cruz In-Silico PCR program to ensure that the PCR primers were not homologous to pseudogene sequences. Primers were designed around the introns.

Example 2

Drug Treatments Reduce Tongue Tumor Development

Figure 7:
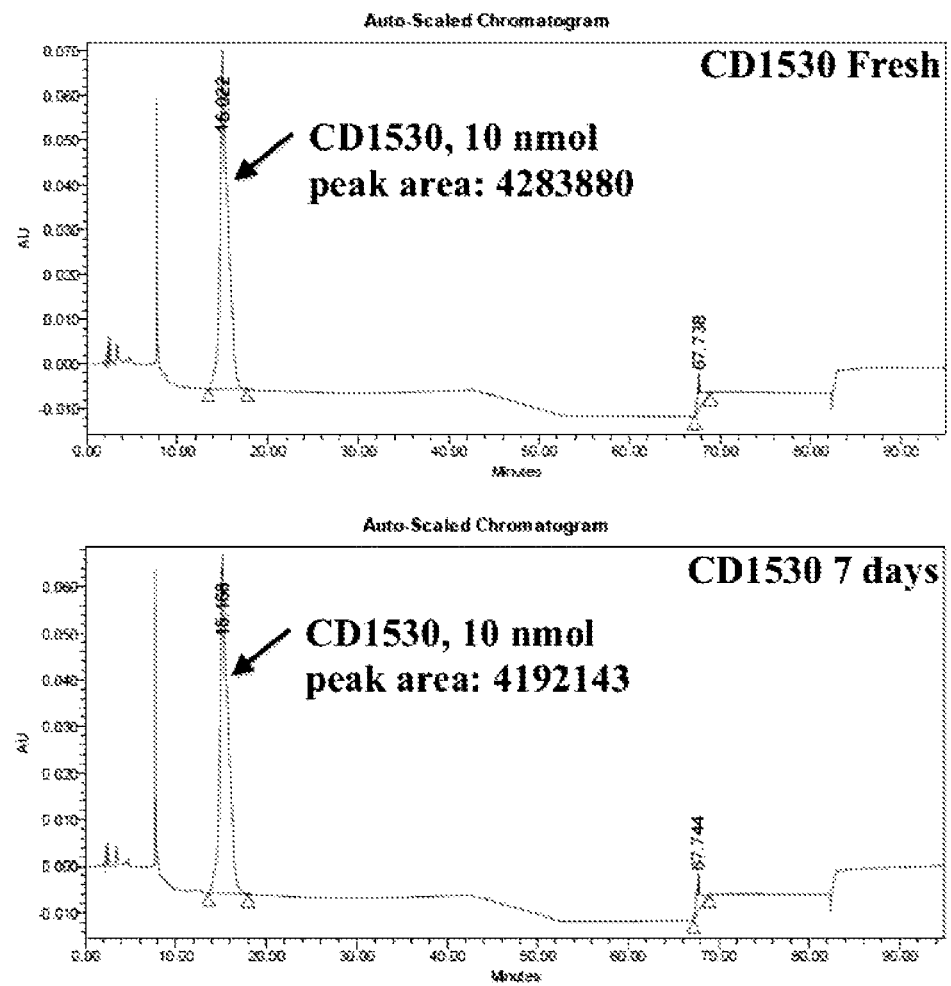
FIG. 7. CD1530 is stable in the drinking water for at least 7 days at room temperature. CD1530 was first dissolved in 100% DMSO and subsequently diluted in the drinking water (the final concentration of DMSO was 0.8%). The same amounts of the freshly prepared CD1530 containing drinking water and the CD1530 containing water prepared 7 days earlier and stored at the room temperature were subjected to high-performance liquid chromatography (HPLC) analysis.

Drug treatments reduce tongue tumor development. All of the mice tolerated the 10 week 4-NQO treatment, and almost all of the mice survived the 15 week post 4-NQO treatment period (A). We determined that the CD1530 in the regular drinking water was stable for at least 7 days at room temperature by HPLC analysis (FIG. 7); thus, we decided to use drinking water as a delivery method because this method is effective and less laborious. During the 15 week post 4-NQO treatment, consumption of regular drinking water and the water that contained CD1530 by the 4-NQO treated mice was comparable, and the consumption of regular diet and bexarotene containing diet by 4-NQO treated mice was also comparable.

Figure 1D:
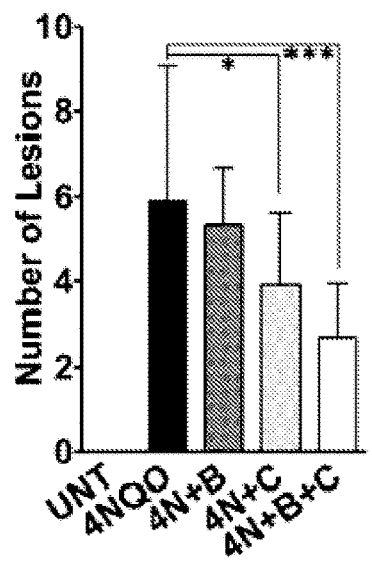

No visible lesions (grade 0) developed in the untreated (UNT) mouse tongues (FIG. 1A). However, we observed obvious multifocal, precancerous, and cancerous lesions during the 15 week post-4-NQO treatment period in all 4-NQO treated mice (1B). Pathological analyses show that after 4-NQO treatment mice developed cancerous lesions, ranging from hyperplasia to malignant squamous cell carcinomas (FIG. 1C), consistent with our previous findings (Tang X H, Albert M, Scognamiglio T, & Gudas L J, (2009), Cancer Prev Res (Phila Pa.) 2(12):1100-1110; Tang X H, Knudsen B, Bemis D, Tickoo S, & Gudas L J, 2004, Clin Cancer Res 10(1 Pt 1):301-313; Tang X H, Su D, Albert M, Scognamiglio T, & Gudas L J, 2009, Cancer Biol Ther 8(13):1214-1225.). The examination of gross tongue lesion multiplicity revealed that compared to an average of 5.9±3.2 tongue lesions observed in the 4-NQO (4-NQO) group, the 4-NQO+bexarotene (4N+B) group developed 5.3±1.4 (p>0.05) tongue lesions, the 4-NQO+CD1530 (4N+C) group developed significantly fewer (3.9±1.7, p<0.05) tongue lesions, and the 4-NQO+bexarotene+CD1530 (4N+B+C) group developed only 2.7±1.2 (p<0.001) tongue lesions, a significantly lower number (FIG. 1D).

Figure 1E:
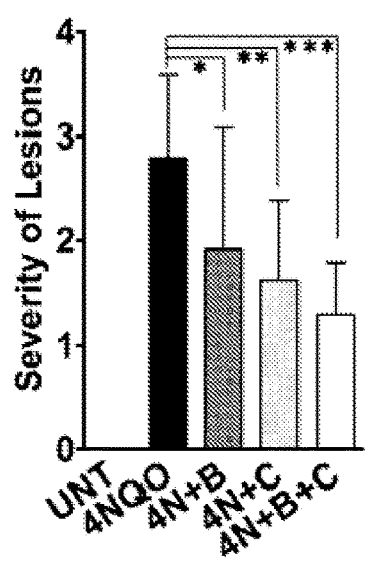

In addition, in the 4-NQO group the severities of all tongue lesions were at or greater than grade 2 and the average severity was 2.8±0.8. The 4N+B group showed an average severity of 1.9±1.2 (p<0.05), with 50% of the lesions at grade 1. The 4N+C group showed an average severity of 1.6±0.8 (p<0.01). In the 4N+B+C group no lesion severity grade was greater than 2, 70% of the lesions were at grade 1, and the average lesion severity was 1.3±0.5 (p<0.001) (FIG. 1E).

Example 3

Bexarotene and CD1530 do not elevate serum triglyceride levels. We also examined the effects of this drug combination on the triglyceride levels in serum samples, because elevated triglyceride levels are associated with cardiovascular risks, which could be a major side-effect in terms of a long term cancer prevention approach. Compared to the UNT group, treatment for 15 weeks with CD1530 alone, bexarotene alone, and the CD1530 plus bexarotene combination did not change serum triglyceride levels significantly (FIG. 2), suggesting that these treatments do not elevate serum triglyceride levels.

Example 4

Figure 8A:
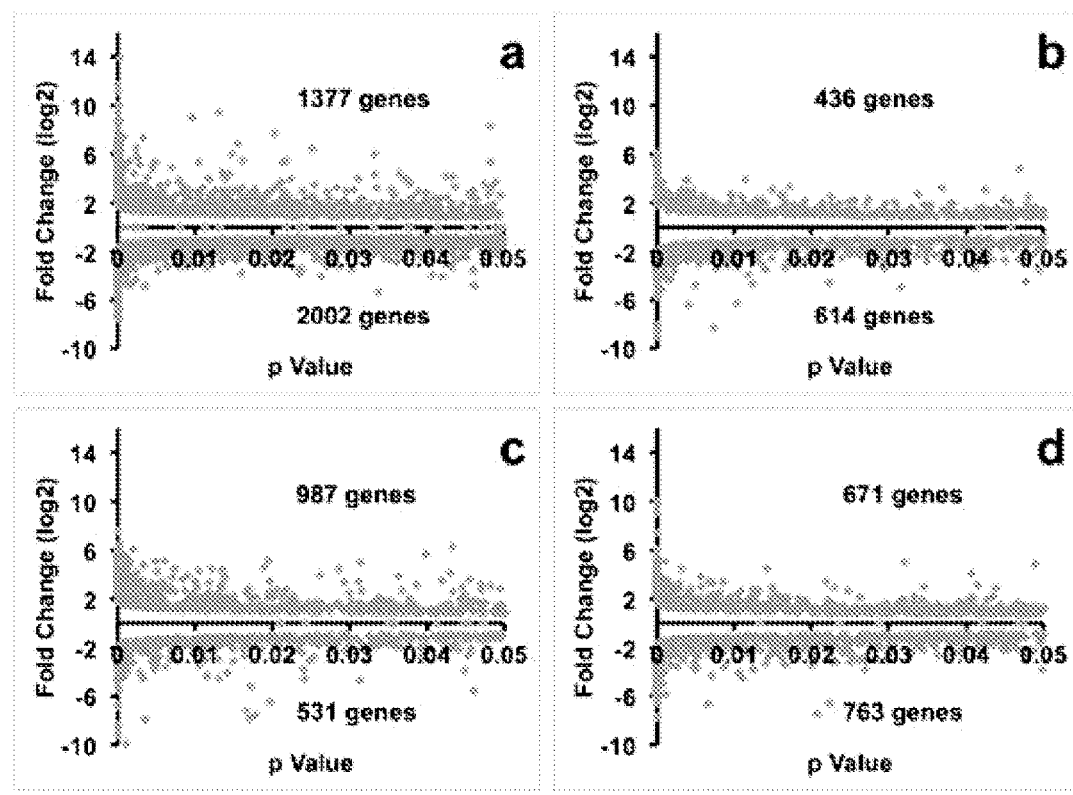
FIG. 8. Global view of alterations in transcript levels by RNA-Seq. The mRNA samples extracted from tongues were subjected to RNA-Seq analysis. A. Total numbers of genes with statistically significant increases or decreases (p<0.05) between any two groups: a, compared to the untreated group, the number of genes changed in the 4-NQO group; b, compared to the 4-NQO group, the number of genes changed in the 4N+B group; c, compared to the 4-NQO group, the number of genes changed in the 4N+C group; d, compared to the 4-NQO group, the number of genes changed in the 4N+B+C group. B. Heat map analyses among all groups of the 3379 genes whose transcript levels statistically differed between the UNT group and the 4-NQO group. UNT, untreated group; 4-NQO, 4-NQO induced tumor group; 4N+B, 4-NQO+bexarotene group; 4N+C, 4-NQO+CD1530 group; 4N+B+C, 4-NQO+bexarotene+CD1530 group. Red, increased transcript levels; green, decreased transcript levels. Color key is defined as (X-mean)/standard deviation, X: a transcript level in a group, mean and standard deviation were the mean and standard deviation of these 5 groups.
Figure 8B:
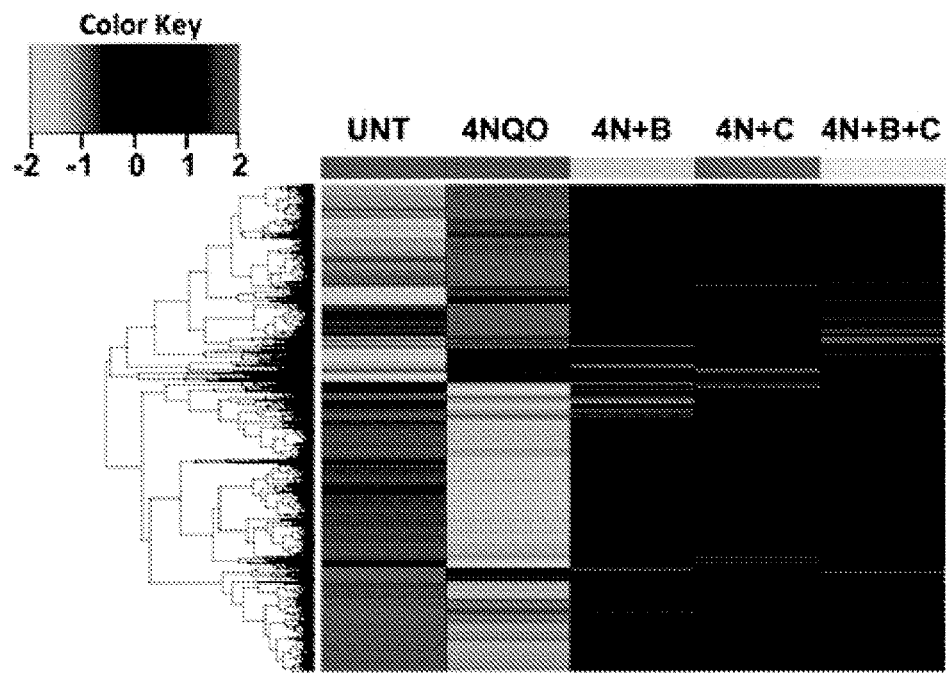

Drug treatments attenuate 4-NQO induced gene expression changes. We next performed RNA-Seq using tongue samples that contained large tumors in the 4-NQO group compared to tongue samples from untreated mice to assess global changes in mRNA expression profiles. We found that the mRNA levels of a total of 3379 genes were significantly over-expressed or under-expressed in the 4-NQO induced tongue tumors vs untreated tongues, including increases in 1377 and decreases in 2002 genes (FIG. 8Aa). Compared to the 4-NQO group, the transcript levels of 1050 genes were significantly different in the 4N+B group (436 with increased and 614 with decreased levels) (FIG. 8Ab); 1518 transcripts were significantly differentially expressed in the 4N+C group (987 genes with greater and 531 genes with lower mRNA levels) (FIG. 8Ac); and 671 transcripts showed higher levels and 763 transcripts showed lower levels in the 4N+B+C group (FIG. 8Ad). Heatmap analysis of the total of 3379 transcripts that differed between the UNT group and the 4-NQO group revealed that to some extent all drug treatments mitigated the effects of 4-NQO on the transcript levels of the majority of these genes (FIG. 8B).

Example 5

Figure 9A:
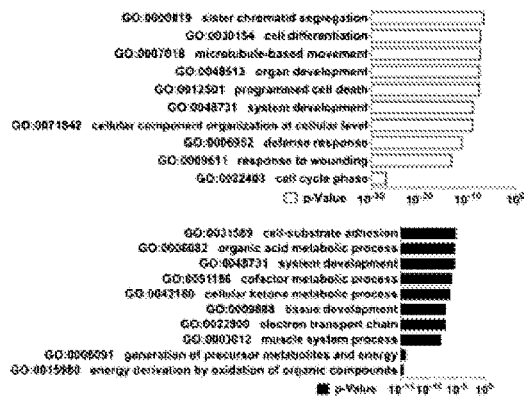
FIG. 9. Gene Ontology (GO) analyses of the genes that show differences (p<0.05) between different groups. White bars indicate categories with increases and black bars show categories with decreases. A. The 4-NQO group compared to the UNT group. B. The 4N+B group compared to the 4-NQO group. C. The 4N+C group compared to the 4-NQO group. D. The 4N+B+C group compared to the 4-NQO group. UNT, untreated; 4-NQO, 4-NQO treatment; 4N+B, 4-NQO+bexarotene; 4N+C, 4-NQO+CD1530; 4N+B+C, 4-NQO+bexarotene+CD1530.

Gene ontology (GO) analysis. Gene ontology (GO) analysis (p-value cutoff: 0.00001), using the ConsensusPathDB online tool, was conducted on the Gene Ontology level 3 of the "Biological Process" domain that has predefined, functional sets for enrichment analysis with default parameter settings. GO analysis revealed that among the top categories with obvious over-representation in the 4-NQO induced tongue tumors vs. untreated tongues were "cell cycle phase" and "cellular component organization at cellular level" (including increases in ECM component degradation enzymes) (FIG. 9A, white bars). Under-expressed GO categories in the 4-NQO induced tongue tumors vs. untreated tongues included "energy derivation by oxidation of organic compounds", "generation of precursor metabolites and energy", and "electron transport chain" (FIG. 9A, black bars), indicating that the transcript levels of the genes in the tricarboxylic acid cycle (TCA) cycle and oxidative phosphorylation (OX-PHOS) pathway were decreased in tongue tumors from the 4-NQO treated group compared to tongues from untreated mice.

Figure 9C:
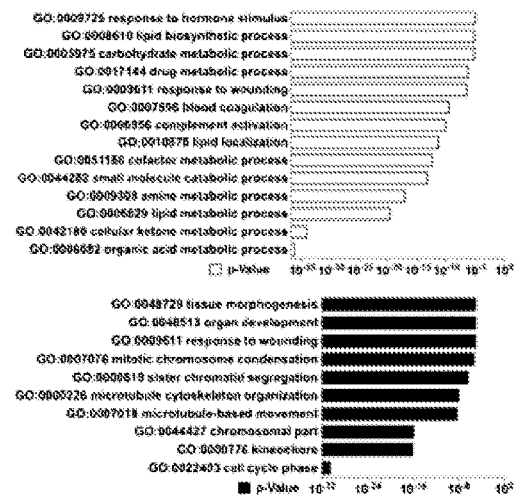
Figure 9B:
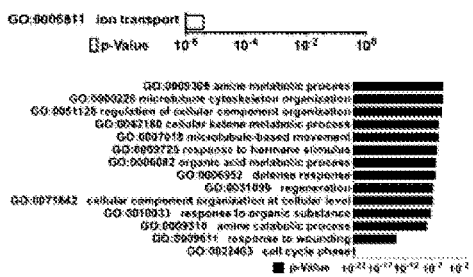
Figure 9D:
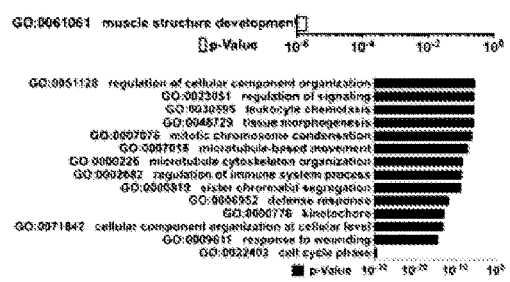

The comparisons between the 4-NQO group and all 4-NQO plus drug treatment groups (4N+B, 4N+C, and 4N+B+C) demonstrated that the GO categories related to cell cycle, DNA replication, and mitosis were statistically the most under-expressed in the three 4-NQO plus drug treatment groups (FIG. 9B-D, black bars). The 4N+C group showed over-representation of many GO categories, with some of them involved in lipid metabolism (FIG. 9C, white bars).

Pathway analysis. Furthermore, pathway enrichment analysis using the ConsensusPathDB online tool (p<0.00001) on the 3379 transcripts with altered levels in the 4-NQO induced tongue tumors was carried out. Similar to the GO analysis, the results suggest that changes in gene expression in the 4-NQO induced tumors compared to the UNT group are broad and reflect the characteristics of these tumor cells, such as enhanced cell proliferation and mobility and abnormal metabolism (Table 1). In addition to the cell cycle related pathways that were down-regulated in the three 4-NQO plus drug treatment groups compared to the 4-NQO group (Table 2-4), the cytochrome P450 enzymes were significantly elevated only in the 4N+C group (Table 3).

Example 6

Figure 10:
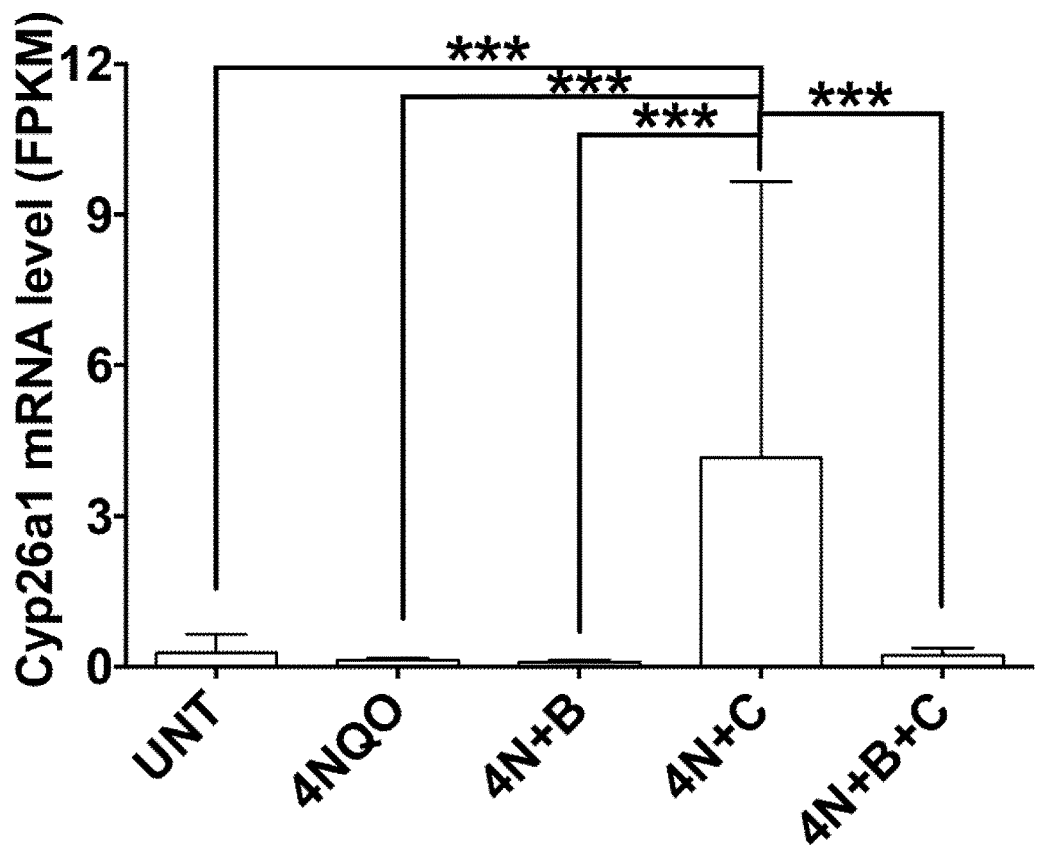
FIG. 10. Quantitative analysis of Cyp26a1 transcripts from the RNA-Seq results (UNT, n=5; 4-NQO, n=3; 4N+B, n=4; 4N+C, n=4; 4N+B+C, n=5; *, p<0.05; , p<0.01; *, p<0.001). UNT, untreated; 4-NQO, 4-NQO treatment; 4N+B, 4-NQO+bexarotene; 4N+C, 4-NQO+CD1530; 4N+B+C, 4-NQO+bexarotene+CD1530.
Figure 11A:
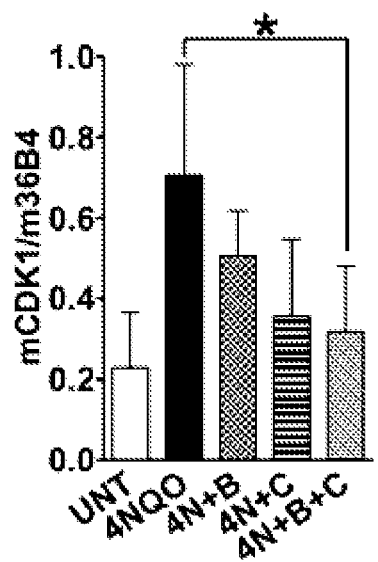
FIG. 11. Real time PCR analysis on the mRNA levels of CDK1 and Cyclin B1 in mouse tongues (UNT, n=5; 4-NQO, n=3; 4N+B, n=4; 4N+C, n=4; 4N+B+C, n=5; *, p<0.05). The RNA samples used for RNA-Seq were used for the real time PCR analysis. A, CDK1; B, Cyclin B1. UNT, untreated; 4-NQO, 4-NQO treatment; 4N+B, 4-NQO+bexarotene; 4N+C, 4-NQO+CD1530; 4N+B+C, 4-NQO+bexarotene+CD1530.
Figure 11B:
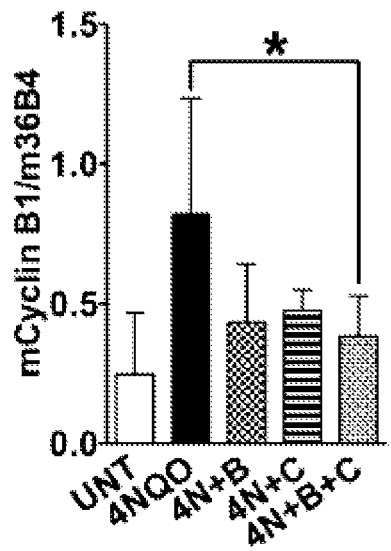

Comparison of mRNA levels of individual genes that play important roles in the pathways described above. As described above, the 4-NQO treatment affected some GO categories and pathways. We then compared the mRNA levels of some individual genes that are important in the GO categories and pathways described above and whose mRNA levels were significantly different between the UNT group and the 4-NQO group. First, we analyzed the transcript levels of Cyp26a1, one member of the cytochrome P450 enzyme family and a direct target of RARγ (Gillespie R F & Gudas L J, 2007, *J Biol Chem* 282(46):33421-33434.). We found that the Cyp26a1 mRNA level was about 20-fold greater in the 4N+C group than in other groups (FIG. 10), indicating that the CD1530 administered to mice specifically transcriptionally activated RARγ target genes.

Figure 3A:
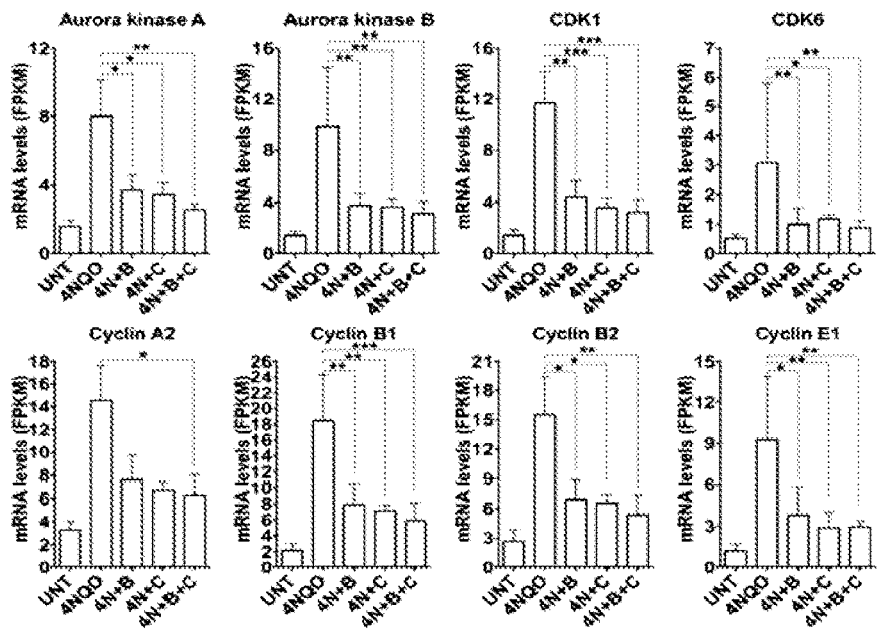
FIG. 3. Quantitative analysis of the transcripts identified as involved in cell proliferation from RNA-Seq data. A. Genes involved in cell cycle regulation. B. Genes involved in DNA replication. DNA2, DNA replication helicase 2; LIG1, DNA ligase 1; FPKM, Fragments Per Kilobase of exon model per Million mapped reads; MCM, minichromosome maintenance complex; ORC1, origin recognition complex subunit 1, POLA1, DNA polymerase, alpha 1; PRIM2, DNA primase large subunit. Differences with p values of <0.05 between the 4-NQO and the 4N+B, 4N+C, 4N+B+C groups were considered statistically significant (UNT, n=5; 4-NQO, n=3; 4N+B, n=4; 4N+C, n=4; 4N+B+C, n=5; *, $p<0.05$; , $p<0.01$; *, $p<0.001$). UNT, untreated; 4-NQO, 4-NQO treatment; 4N+B, 4-NQO+bexarotene; 4N+C, 4-NQO+CD1530; 4N+B+C, 4-NQO+bexarotene+CD1530.

One of the characteristics of tumor development is cell cycle progression, the transition from the G1 phase to the S, G2, and M phases of the cell cycle (Sherr C J, 2004, *Cell* 116:235-246.). With respect to the transcript levels of genes involved in cell cycle progression, only aurora kinase A and B, CDK 1 and 6, and cyclin A2, B1, B2 and E1 (Malumbres M & Barbacid M, 2005, *Trends Biochem Sci* 30(11):630-641; Sherr C J, 2000, *Harvey Lect* 96:73-92.) levels were significantly greater in the 4-NQO group than in the UNT tongues. Compared to the 4-NQO group, these transcript levels were significantly lower in all 4-NQO plus drug treatment groups except for cyclin A2, which was significantly lower only in the 4N+B+C group (FIG. 3A). These data correlate with our data on tumor multiplicity and severity.

Figure 3B:
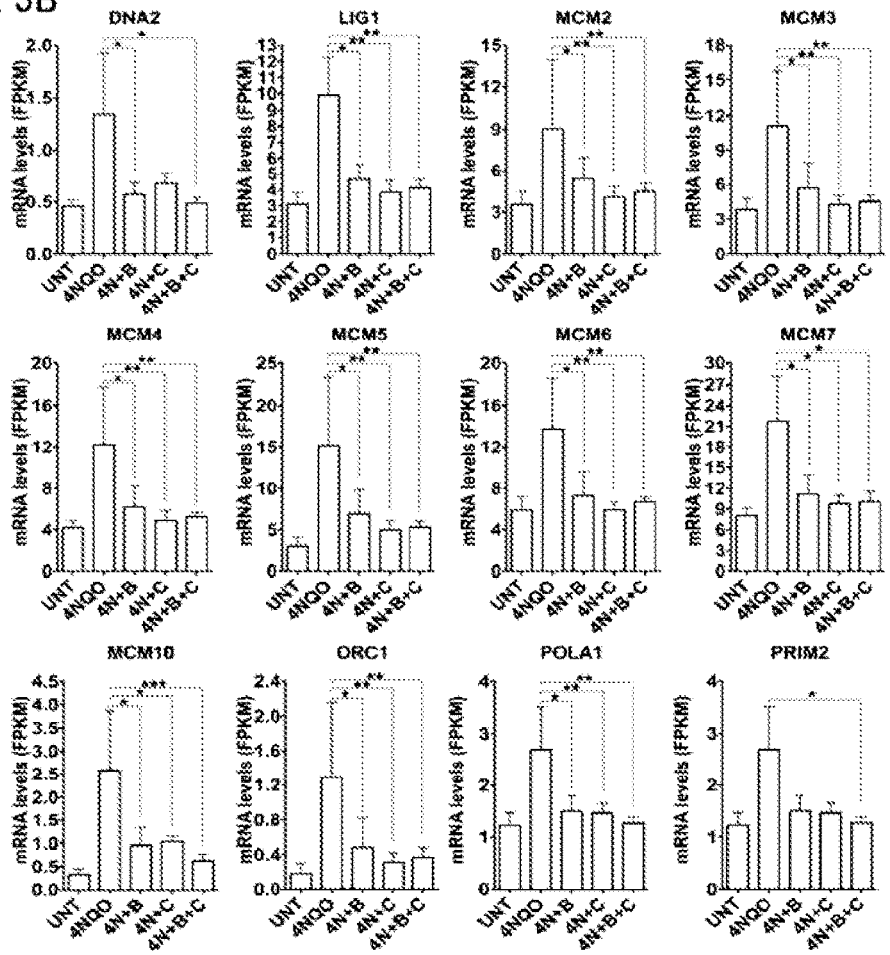

Compared to the UNT samples, transcripts involved in DNA replication were also significantly increased in the 4-NQO group, including minichromosome maintenance (MCM) complex members 2-7 and 10 that unwind the double stranded DNA at the origins, recruit DNA polymerases, and initiate DNA synthesis (Maiorano D, Lutzmann M, & Méchali M, 2006, *Curr Opin Cell Biol* 18(2):130-136.); DNA replication helicase 2 (DNA2), a key enzyme involved in DNA replication and DNA repair in both the nucleus and mitochondria; DNA ligase 1 (LIG1); origin recognition complex, subunit 1 (ORC1); DNA polymerase, alpha 1 (POLA1), the catalytic subunit of DNA polymerase; and DNA primase large subunit (PRIM2). The 4N+B, 4N+C, and 4N+B+C groups showed significantly lower transcript levels of the majority of these genes as compared to the 4-NQO group, especially the 4N+B+C group, in which the mRNA levels of all of these genes were greatly reduced (FIG. 3B).

Matrix metalloproteinases (MMP) contribute to extracellular matrix (ECM) breakdown and cancer cell migration (Munshi H G & Stack M S, 2006, *Cancer Metastasis Rev* 25(1):45-56.), and tenascin C (TNC) is involved in cell migration (Orend G & Chiquet-Ehrismann R, 2006, *Cancer Lett* 244(2):143-163.). We found that the transcript levels of MMPs 3, 9, 10, 12-14, and TNC were significantly elevated in the 4-NQO group compared to the UNT group. We also showed that all 4-NQO plus drug treatment groups displayed significant lower mRNA levels of the majority of these genes and that 4N+B+C drug combination reduced the levels of transcripts (FIG. 4A).

Figure 4C:
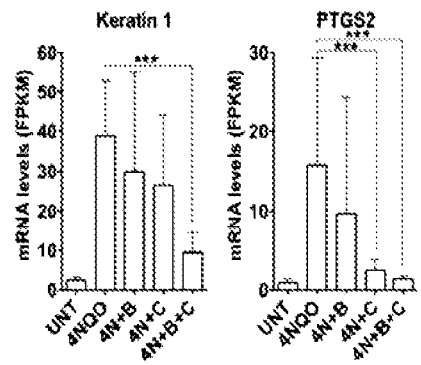
Figure 12A:
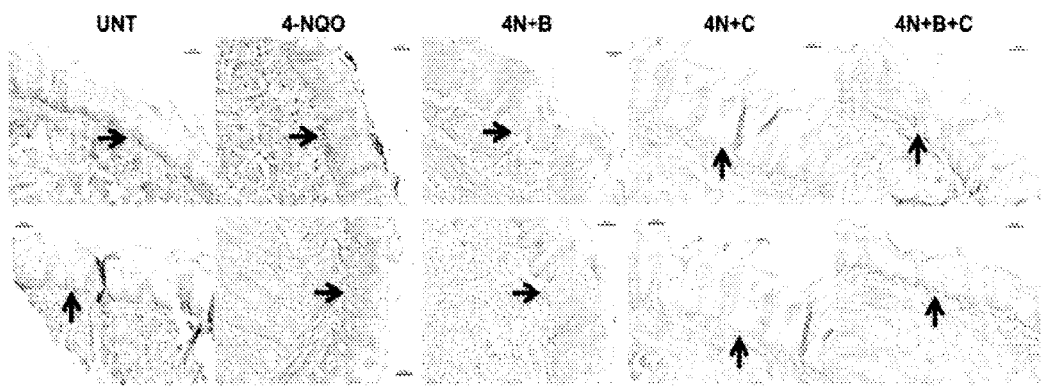
FIG. 12. IL-6 and MCT4 proteins (arrows) in tongue epithelium. Antibody staining of two samples/groups of tongue sections: A. IL-6. B. MCT4. UNT, untreated; 4-NQO, 4-NQO treatment; 4N+B, 4-NQO+bexarotene; 4N+C, 4-NQO+CD1530; 4N+B+C, 4-NQO+bexarotene+CD1530.
Figure 12B:
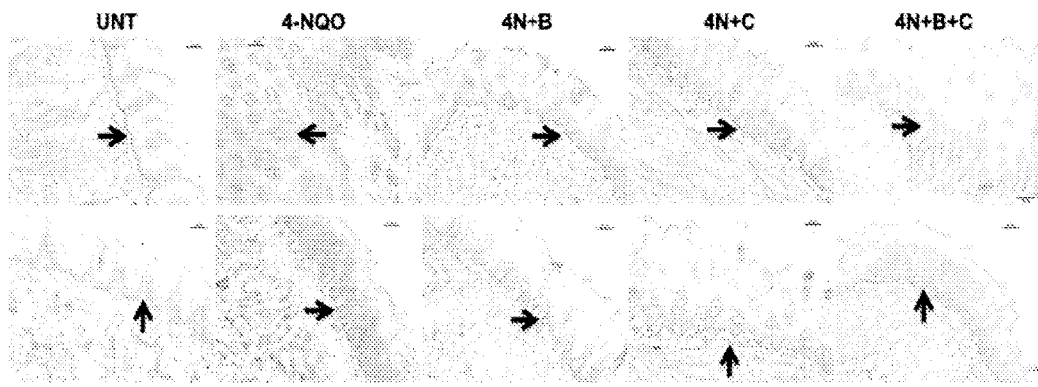

Hypoxia-inducible factor 1α (HIF1α) is involved in the switch from tricarboxylic acid (TCA) cycle and oxidative phosphorylation (OX-PHOS) pathways to glycolysis (Aragonés J, Fraisl P, Baes M, & Carmeliet P, 2009, *Cell Metab* 9(1):11-22.). Because we observed significantly decreased mRNA levels of many genes of the TCA cycle and oxidative phosphorylation, we ascertained the transcript levels of HIF1α and several HIF1α targets that participate in the modulation of glycolysis and oxidative phosphorylation, such as glucose transporter 1 (GLUT1) (Brahimi-Horn M C, Bellot G, & Pouysségur J, 2011, *Curr Opin Genet Dev* 21(1):67-72.), monocarboxylate transporter 4 (Slc16a3, MCT4) (31), and NADH dehydrogenase (ubiquinone) 1 alpha subcomplex, 4-like (Ndufa4l2) that inhibits oxidative phosphorylation (Tello D, et al., 2011, *Cell Metab* 14(6):768-779.). Transcripts of HIF1α and its targets, described above, were significantly increased in the 4-NQO group compared to the UNT group, and the mRNA levels of these genes in the 4N+B+C group were significantly lower than in the 4-NQO group (FIG. 4B). In addition, low MCT4 protein was detected in the basal layer of tongue epithelium in the UNT samples (FIG. 12B, arrows), and the 4-NQO treatment resulted in both an increase in the MCT4 protein level and an expansion of MCT4 staining to the suprabasal layers of the tongue epithelium (FIG. 12B). Compared to the 4-NQO group, all 4-NQO plus drug treatment groups (4N+B, 4N+C, and 4N+B+C) showed lower MCT4 protein levels in the tongue epithelium (FIG. 12B). Moreover, the transcript levels of oral cancer markers, such as keratin 1 (Tang X H, Knudsen B, Bemis D, Tickoo S, & Gudas L J, 2004, *Clin Cancer Res* 10(1 Pt 1):301-313.) and prostaglandin-endoperoxide synthase 2 (PTGS2), also known as cyclooxygenase-2 (COX-2) (Khan Z, et al., 2011, *Curr Drug Targets* 12(7):1082-1093.), were significantly lower in the 4N+B+C group than the 4-NQO group (FIG. 4C).

Additionally, we performed quantitative real time PCR on some of the genes described above to validate the RNA-Seq data (FIG. S5). Collectively, the RNA-Seq data analyses correlate with the tongue tumor multiplicity and severity data (FIG. 1D, E), suggesting that the drug treatments, especially the combination of bexarotene and CD1530, may suppress/reduce tongue carcinogenesis via reduction of transcript levels of genes involved in cell cycle progression and cell migration.

Example 7

Oxidative stress level, as assessed by 4-hydroxynoneal (4-HNE), is lower in the tongues from the 4-NQO and subsequent drug treatment groups. Excessive reactive oxygen species (ROS) accumulation, caused by carcinogen exposure, may play a role in human oral carcinogenesis because ROS causes oxidative modifications of cellular macromolecules such as DNA, proteins, and lipids (33). Therefore, we next examined the levels of 4-hydroxynonenal (4-HNE), an $\alpha,\beta$-unsaturated hydroxyalkenal that is produced by lipid peroxidation in cells during oxidative stress, and is a marker of oxidative stress caused by reactive oxygen species (ROS) (Ullery J C & Marnett L J, 2012, *Biochim Biophys Acta* 1818(10):2424-2435.). The 4-NQO samples showed a large increase in the 4-FINE levels in the precancerous tongue epithelium (top panel) and cancerous lesions (bottom panel) compared to the UNT samples (FIG. 5). It is important to note that these 4-NQO samples were assessed for 4-HNE levels 17 weeks after the cessation of the 4-NQO administration, indicating that a higher ROS level is a lasting feature of carcinogen treatment. Moreover, the tongue samples from the 4N+B, 4N+C, and 4N+B+C groups exhibited lower 4-1-INE levels than those from the 4-NQO group (FIG. 5), indicating that the treatments with bexarotene, CD1530, and bexarotene plus CD1530 resulted in lower oxidative stress. The lower oxidative stress, as assessed by lower 4-FINE levels (FIG. 5), may be one of the mechanisms through which the retinoid drug treatments reduced oral carcinogenesis, though further testing is required.

Example 8

Figure 6A:
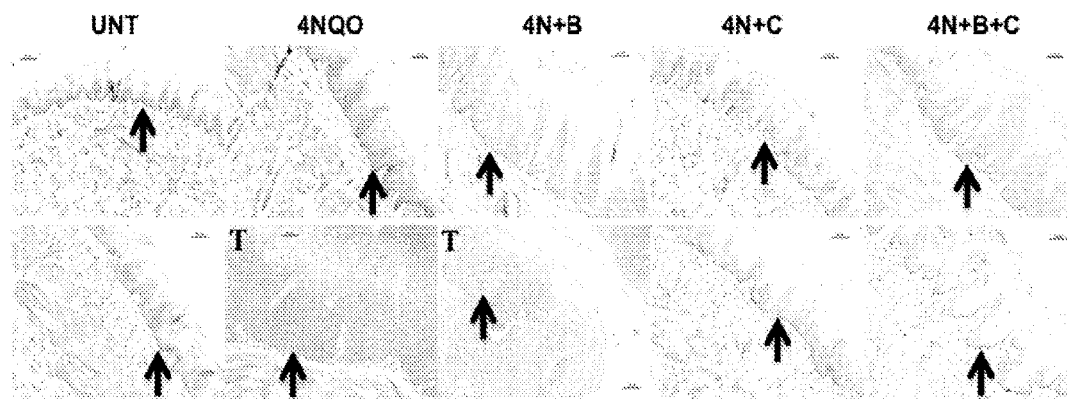
FIG. 6. β-catenin and MMP9 proteins in tongue epithelium. The tongues were fixed, embedded in paraffin, and sectioned. Then the tissue sections were stained with various antibodies (magnification, 200×). Four to five representative areas of each tongue section from two to four mice/group were photographed and analyzed. A. β-catenin B. MMP9. Two samples/group are shown. UNT, untreated; 4-NQO, 4-NQO treatment; 4N+B, 4-NQO+bexarotene; 4N+C, 4-NQO+CD1530; 4N+B+C, 4-NQO+bexarotene+CD1530. T, tumor.

$\beta$-Catenin levels are lower in the tongues from the 4-NQO and subsequent drug treatment groups compared to the 4-NQO group. Oxidative stress can activate the $\beta$-catenin/Wnt signaling pathway (Reuter S, Gupta S C, Chaturvedi M M, & Aggarwal B B, 2010, *Free Radic Biol Med* 49(11): 1603-1616.). and the increase in $\beta$-catenin protein level can lead to increased cell proliferation in human head and neck cancer cells (Song J, Chang I, Chen Z, Kang M, & Wang C Y, 2010, *PLoS One* 5(7):e11456.). Increased $\beta$-catenin levels have been observed during human oral squamous cell carcinoma development (Pannone G, et al., 2010, *Oncol Rep* 24(4):1035-1041.). We detected $\beta$-catenin protein primarily in the basal layer of tongue epithelium in the UNT samples (FIG. 6A, arrows), and 4-NQO treatment resulted in both an increase in the $\beta$-catenin level and an expansion of $\beta$-catenin staining to the suprabasal layers of the tongue epithelium (top panel) and tumors (bottom panel) (FIG. 6A), consistent with our previous findings (Osei-Sarfo K, Tang X H, Urvalek A M, Scognamiglio T, & Gudas L J, 2013, *Carcinogenesis* 34(11):2673-2681.). Compared to the 4-NQO group, all 4-NQO plus drug treatment groups (4N+B, 4N+C, and 4N+B+C) showed lower $\beta$-catenin protein levels in the tongue epithelium, primarily limited to the basal layer, even in the regions of tumor (bottom panel) (FIG. 6A).

Example 9

Figure 6B:
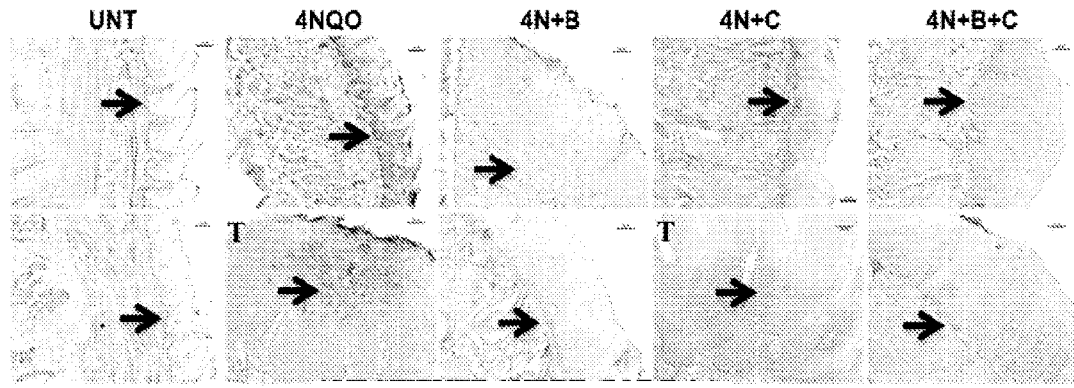

All drug treatments result in lower MMP9 protein levels. High matrix metalloproteinase 9 (MMP9) protein levels have been observed in human oral cancers, and MMP9 is a marker of malignant human oral cancer (Fan H X, Li H X, Chen D, Gao Z X, & Zheng J H, 2012, *J Exp Clin Cancer Res* 31:90; Patel B P, Shah S V, Shukla S N, Shah P M, & Patel P S, 2007, *Head Neck* 29(6):564-572.). We discovered that the MMP9 protein levels were low in untreated tongue epithelium, and that 4-NQO treatment resulted in an increase in MMP9 protein levels in tongue epithelium and tongue tumors (bottom panel) (FIG. 6B). All 4-NQO plus drug treatment groups showed lower MMP9 protein levels in tongue epithelia compared to the 4-NQO group (FIG. 6B). Combined with the RNA-Seq data on the pathways of ECM breakdown and cell migration (FIG. 4A), our data indicate that the retinoid drug treatments limited the breakdown of ECM and potentially reduced cell migration and metastasis.

Example 10

The tongues were fixed, embedded in paraffin, and sectioned. Then the tissue sections were stained with various antibodies (magnification, 200×). Four to five representative areas of each tongue section from two to four mice/group were photographed and analyzed (FIGS. 12A and 12B). Interleukin-6 (IL-6) is a multifunctional cytokine that is involved in the regulation of immune responses and cellular functions. IL-6 levels are enhanced in human oral squamous cell carcinoma and IL-6 is considered a bad prognostic factor in this cancer (Expert Opin Ther Targets. 2013 January; 17(1):53-9). IL-6 protein was detected primarily in the basal layer of tongue epithelium in the UNT samples (FIG. 12A, arrows), but in the 4-NQO treated samples we observed both an increase in the protein level and an expansion of IL-6 signal to the suprabasal layers of the tongue epithelium (FIG. 12A). Compared to the 4-NQO group, all 4-NQO plus drug treatment groups (4N+B, 4N+C, and 4N+B+C) showed lower IL-6 protein levels in the tongue epithelium (FIG. 12A).

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

TABLE 1

Pathways significantly differed in the 4-NQO group vs. the Control group

| pathway name | set size | candidates contained | p-value | q-value | pathway source |
|---|---|---|---|---|---|
| Down-regulated in 4-NQO group vs. Control group | | | | | |
| Metabolism | 1039 | 173 (17.8%) | 1.01E−19 | 5.96E−17 | Reactome |
| Valine, leucine and isoleucine degradation-*Mus musculus* (mouse) | 50 | 28 (56.0%) | 7.19E−17 | 2.13E−14 | KEGG |
| Pyruvate metabolism and Citric Acid (TCA) cycle | 36 | 23 (65.7%) | 2.96E−16 | 5.83E−14 | Reactome |
| The citric acid (TCA) cycle and respiratory electron transport | 153 | 44 (34.4%) | 1.81E−15 | 2.68E−13 | Reactome |
| Mitochondrial Fatty Acid Beta-Oxidation | 15 | 14 (100.0%) | 2.72E−15 | 3.21E−13 | Reactome |
| Fatty acid, triacylglycerol, and ketone body metabolism | 66 | 28 (43.8%) | 2.59E−13 | 2.55E−11 | Reactome |
| Propanoate metabolism-*Mus musculus* (mouse) | 33 | 19 (59.4%) | 1.76E−12 | 1.49E−10 | KEGG |
| Citrate cycle (TCA cycle)-*Mus musculus* (mouse) | 31 | 18 (58.1%) | 1.17E−11 | 8.61E−10 | KEGG |
| Branched-chain amino acid catabolism | 17 | 13 (76.5%) | 5.04E−11 | 3.31E−09 | Reactome |
| Metabolic pathways-*Mus musculus* (mouse) | 1212 | 172 (14.5%) | 8.91E−11 | 5.27E−09 | KEGG |
| Citric acid cycle (TCA cycle) | 18 | 13 (72.2%) | 1.66E−10 | 8.94E−09 | Reactome |
| valine degradation | 15 | 11 (73.3%) | 3.54E−09 | 1.74E−07 | MouseCyc |
| mitochondrial fatty acid beta-oxidation of saturated fatty acids | 9 | 8 (100.0%) | 4.89E−09 | 2.22E−07 | Reactome |
| Fatty acid metabolism-*Mus musculus* (mouse) | 49 | 19 (38.8%) | 2.11E−08 | 8.90E−07 | KEGG |
| Vascular smooth muscle contraction-*Mus musculus* (mouse) | 123 | 32 (26.2%) | 2.85E−08 | 1.12E−06 | KEGG |
| Salivary secretion-*Mus musculus* (mouse) | 77 | 24 (31.2%) | 4.45E−08 | 1.64E−06 | KEGG |
| Dilated cardiomyopathy-*Mus musculus* (mouse) | 91 | 26 (29.2%) | 5.42E−08 | 1.88E−06 | KEGG |
| Pyruvate metabolism | 19 | 11 (61.1%) | 6.37E−08 | 2.09E−06 | Reactome |
| Regulation of pyruvate dehydrogenase (PDH) complex | 12 | 9 (75.0%) | 7.58E−08 | 2.36E−06 | Reactome |
| fatty acid £]-oxidation I | 28 | 13 (48.1%) | 1.77E−07 | 5.24E−06 | MouseCyc |
| TCA cycle variation III (eukaryotic) | 16 | 10 (62.5%) | 1.93E−07 | 5.44E−06 | MouseCyc |
| Respiratory electron transport | 97 | 23 (29.5%) | 2.64E−07 | 7.09E−06 | Reactome |
| Calcium signaling pathway-*Mus musculus* (mouse) | 180 | 38 (21.3%) | 5.33E−07 | 1.37E−05 | KEGG |
| Bile secretion-*Mus musculus* (mouse) | 71 | 21 (29.6%) | 8.25E−07 | 2.03E−05 | KEGG |
| aerobic respiration--electron donor II | 101 | 23 (27.4%) | 1.13E−06 | 2.68E−05 | MouseCyc |
| isoleucine degradation | 15 | 9 (60.0%) | 1.34E−06 | 2.94E−05 | MouseCyc |
| Respiratory electron transport, ATP synthesis by chemiosmotic coupling, and heat production by uncoupling proteins. | 121 | 25 (25.8%) | 1.34E−06 | 2.94E−05 | Reactome |
| Muscle contraction | 47 | 16 (34.0%) | 2.16E−06 | 4.42E−05 | Reactome |
| Parkinson,s disease-*Mus musculus* (mouse) | 149 | 30 (22.7%) | 2.17E−06 | 4.42E−05 | KEGG |
| Hypertrophic cardiomyopathy (HCM)-*Mus musculus* (mouse) | 83 | 22 (26.5%) | 3.49E−06 | 6.88E−05 | KEGG |
| aerobic respiration--electron donors reaction list | 7 | 6 (85.7%) | 3.80E−06 | 7.25E−05 | MouseCyc |
| TCA cycle | 13 | 8 (61.5%) | 4.13E−06 | 7.64E−05 | MouseCyc |
| Alzheimer,s disease-*Mus musculus* (mouse) | 189 | 36 (20.1%) | 4.62E−06 | 8.27E−05 | KEGG |
| Gastric acid secretion-*Mus musculus* (mouse) | 73 | 20 (27.4%) | 5.59E−06 | 9.71E−05 | KEGG |
| Beta oxidation of lauroyl-CoA to decanoyl-CoA-CoA | 6 | 5 (100.0%) | 6.45E−06 | 0.0001 | Reactome |
| Beta oxidation of hexanoyl-CoA to butanoyl-CoA | 6 | 5 (100.0%) | 6.45E−06 | 0.0001 | Reactome |
| Beta oxidation of decanoyl-CoA to octanoyl-CoA-CoA | 6 | 5 (100.0%) | 6.45E−06 | 0.0001 | Reactome |
| Beta oxidation of octanoyl-CoA to hexanoyl-CoA | 6 | 5 (100.0%) | 6.45E−06 | 0.0001 | Reactome |
| Striated Muscle Contraction | 26 | 11 (42.3%) | 7.76E−06 | 0.000118 | Reactome |
| Focal adhesion-*Mus musculus* (mouse) | 200 | 38 (19.1%) | 9.10E−06 | 0.000135 | KEGG |
| Cholinergic synapse-*Mus musculus* (mouse) | 115 | 26 (22.8%) | 9.60E−06 | 0.000138 | KEGG |
| UP-regulated in the 4-NQO group vs. the Control group | | | | | |
| DNA Replication | 163 | 59 (37.6%) | 5.05E−27 | 3.15E−24 | Reactome |
| Cell Cycle, Mitotic | 277 | 76 (28.4%) | 1.96E−25 | 4.08E−23 | Reactome |
| Mitotic M-M/G1 phases | 141 | 53 (39.3%) | 1.96E−25 | 4.08E−23 | Reactome |
| Cell Cycle | 314 | 80 (26.3%) | 2.14E−24 | 3.35E−22 | Reactome |
| M Phase | 102 | 38 (38.4%) | 3.93E−18 | 4.90E−16 | Reactome |
| Mitotic Prometaphase | 98 | 36 (37.9%) | 5.00E−17 | 5.20E−15 | Reactome |
| Cell cycle-*Mus musculus* (mouse) | 127 | 33 (26.0%) | 1.66E−10 | 1.48E−08 | KEGG |
| Cytokine-cytokine receptor interaction-*Mus musculus* (mouse) | 245 | 48 (19.6%) | 5.74E−10 | 4.48E−08 | KEGG |
| Cell Cycle Checkpoints | 82 | 24 (31.2%) | 9.92E−10 | 6.88E−08 | Reactome |
| G2/M Checkpoints | 45 | 18 (40.0%) | 1.32E−09 | 8.24E−08 | Reactome |
| Mitotic G1-G1/S phases | 76 | 23 (31.5%) | 1.75E−09 | 9.95E−08 | Reactome |
| Activation of the pre-replicative complex | 29 | 14 (48.3%) | 4.78E−09 | 2.48E−07 | Reactome |
| G1/S Transition | 65 | 20 (32.3%) | 1.29E−08 | 6.20E−07 | Reactome |
| DNA Replication Pre-Initiation | 39 | 15 (41.7%) | 1.65E−08 | 6.86E−07 | Reactome |
| M/G1 Transition | 39 | 15 (41.7%) | 1.65E−08 | 6.86E−07 | Reactome |
| DNA replication-*Mus musculus* (mouse) | 36 | 14 (38.9%) | 1.42E−07 | 5.53E−06 | KEGG |
| Synthesis of DNA | 57 | 17 (31.5%) | 2.40E−07 | 8.81E−06 | Reactome |
| Activation of ATR in response to replication stress | 38 | 14 (36.8%) | 3.13E−07 | 1.09E−05 | Reactome |
| DNA strand elongation | 31 | 12 (38.7%) | 1.20E−06 | 3.93E−05 | Reactome |
| Hematopoietic cell lineage-*Mus musculus* (mouse) | 84 | 20 (24.4%) | 2.05E−06 | 6.18E−05 | KEGG |
| PD-1 signaling | 14 | 8 (57.1%) | 2.08E−06 | 6.18E−05 | Reactome |
| Costimulation by the CD28 family | 57 | 16 (28.6%) | 2.33E−06 | 6.38E−05 | Reactome |
| S Phase | 72 | 18 (26.1%) | 2.35E−06 | 6.38E−05 | Reactome |
| Unwinding of DNA | 11 | 7 (63.6%) | 3.51E−06 | 9.12E−05 | Reactome |
| Removal of licensing factors from origins | 33 | 11 (36.7%) | 6.26E−06 | 0.00015 | Reactome |
| Regulation of DNA replication | 33 | 11 (36.7%) | 6.26E−06 | 0.00015 | Reactome |
| Rheumatoid arthritis-*Mus musculus* (mouse) | 83 | 19 (23.5%) | 6.85E−06 | 0.000158 | KEGG |

TABLE 2

Pathways significantly differed in the 4-NQO + bexarotene group vs. the 4-NQO group

| pathway name | set size | candidates contained | p-value | q-value | pathway source |
|---|---|---|---|---|---|
| Down-regulated in the 4-NQO + Bexarotene group vs. 4-NQO group | | | | | |
| Mitotic M-M/G1 phases | 141 | 32 (23.7%) | 5.44E−17 | 2.22E−14 | Reactome |
| DNA Replication | 163 | 34 (21.7%) | 1.08E−16 | 2.22E−14 | Reactome |
| Cell Cycle, Mitotic | 277 | 44 (16.4%) | 1.75E−16 | 2.39E−14 | Reactome |
| Cell Cycle | 314 | 46 (15.1%) | 8.68E−16 | 8.88E−14 | Reactome |
| Complement and coagulation cascades-*Mus musculus* (mouse) | 76 | 21 (27.6%) | 5.93E−13 | 4.85E−11 | KEGG |
| M Phase | 102 | 22 (22.2%) | 1.95E−11 | 1.33E−09 | Reactome |
| Mitotic Prometaphase | 98 | 21 (22.1%) | 6.32E−11 | 3.70E−09 | Reactome |
| Hemostasis | 305 | 37 (12.3%) | 3.86E−10 | 1.97E−08 | Reactome |
| G2/M Checkpoints | 45 | 13 (28.9%) | 9.29E−09 | 4.22E−07 | Reactome |
| Metabolism of amino acids and derivatives | 127 | 21 (16.9%) | 1.09E−08 | 4.32E−07 | Reactome |
| Lipoprotein metabolism | 32 | 11 (35.5%) | 1.16E−08 | 4.32E−07 | Reactome |
| Platelet degranulation | 65 | 15 (23.4%) | 1.56E−08 | 5.30E−07 | Reactome |
| Cell Cycle Checkpoints | 82 | 16 (20.8%) | 3.24E−08 | 1.02E−06 | Reactome |
| Response to elevated platelet cytosolic Ca2+ | 71 | 15 (21.4%) | 5.68E−08 | 1.66E−06 | Reactome |
| Formation of Fibrin Clot (Clotting Cascade) | 35 | 10 (29.4%) | 4.14E−07 | 1.08E−05 | Reactome |
| Cell cycle-*Mus musculus* (mouse) | 127 | 19 (15.0%) | 4.22E−07 | 1.08E−05 | KEGG |
| Mitotic G1-G1/S phases | 76 | 14 (19.2%) | 6.77E−07 | 1.61E−05 | Reactome |
| DNA Replication Pre-Initiation | 39 | 10 (27.8%) | 7.49E−07 | 1.61E−05 | Reactome |
| M/G1 Transition | 39 | 10 (27.8%) | 7.49E−07 | 1.61E−05 | Reactome |
| Activation of the pre-replicative complex | 29 | 9 (31.0%) | 9.61E−07 | 1.97E−05 | Reactome |
| Activation of ATR in response to replication stress | 38 | 10 (26.3%) | 1.30E−06 | 2.53E−05 | Reactome |
| HDL-mediated lipid transport | 18 | 7 (41.2%) | 1.82E−06 | 3.27E−05 | Reactome |
| Retinol metabolism-*Mus musculus* (mouse) | 79 | 14 (17.7%) | 1.84E−06 | 3.27E−05 | KEGG |
| Lipid digestion, mobilization, and transport | 50 | 11 (22.4%) | 2.13E−06 | 3.62E−05 | Reactome |
| G1/S Transition | 65 | 12 (19.4%) | 3.88E−06 | 6.35E−05 | Reactome |
| Phenylalanine and tyrosine catabolism | 8 | 5 (62.5%) | 4.51E−06 | 7.04E−05 | Reactome |
| Common Pathway | 13 | 6 (46.2%) | 4.65E−06 | 7.04E−05 | Reactome |
| Upregulated in 4-NQO + Bexarotene group vs. 4-NQO group | | | | | |
| Gastric acid secretion-*Mus musculus* (mouse) | 73 | 10 (13.7%) | 1.49E−06 | 0.000265 | KEGG |
| Calcium signaling pathway-*Mus musculus* (mouse) | 180 | 15 (8.4%) | 2.16E−06 | 0.000265 | KEGG |

TABLE 3

Pathways significantly differed in the 4-NQO + CD1530 group vs. the 4-NQO group

| pathway name | set size | candidates contained | p-value | q-value | pathway source |
|---|---|---|---|---|---|
| Downregulated in the 4-NQO + CD1530 group vs. the 4-NQO group | | | | | |
| Cell Cycle, Mitotic | 277 | 52 (19.4%) | 3.45E−28 | 6.72E−26 | Reactome |
| Mitotic M-M/G1 phases | 141 | 39 (28.9%) | 4.19E−28 | 6.72E−26 | Reactome |
| DNA Replication | 163 | 41 (26.1%) | 1.32E−27 | 1.42E−25 | Reactome |
| Cell Cycle | 314 | 54 (17.8%) | 2.80E−27 | 2.25E−25 | Reactome |
| M Phase | 102 | 27 (27.3%) | 5.90E−19 | 3.79E−17 | Reactome |
| Mitotic Prometaphase | 98 | 26 (27.4%) | 2.48E−18 | 1.33E−16 | Reactome |
| Cell Cycle Checkpoints | 82 | 19 (24.7%) | 8.40E−13 | 3.85E−11 | Reactome |
| Cell cycle-*Mus musculus* (mouse) | 127 | 23 (18.1%) | 3.38E−12 | 1.36E−10 | KEGG |
| G2/M Checkpoints | 45 | 14 (31.1%) | 3.01E−11 | 1.07E−09 | Reactome |
| DNA Replication Pre-Initiation | 39 | 12 (33.3%) | 3.25E−10 | 9.48E−09 | Reactome |
| M/G1 Transition | 39 | 12 (33.3%) | 3.25E−10 | 9.48E−09 | Reactome |
| Activation of the pre-replicative complex | 29 | 11 (37.9%) | 3.63E−10 | 9.54E−09 | Reactome |
| Mitotic G1-G1/S phases | 76 | 16 (21.9%) | 3.87E−10 | 9.54E−09 | Reactome |
| G1/S Transition | 65 | 14 (22.6%) | 3.29E−09 | 7.55E−08 | Reactome |
| Assembly of the pre-replicative complex | 25 | 9 (40.9%) | 6.95E−09 | 1.49E−07 | Reactome |
| Activation of ATR in response to replication stress | 38 | 11 (28.9%) | 9.88E−09 | 1.82E−07 | Reactome |
| Removal of licensing factors from origins | 33 | 10 (33.3%) | 1.02E−08 | 1.82E−07 | Reactome |
| Regulation of DNA replication | 33 | 10 (33.3%) | 1.02E−08 | 1.82E−07 | Reactome |
| Unwinding of DNA | 11 | 6 (54.5%) | 3.08E−07 | 5.20E−06 | Reactome |
| Synthesis of DNA | 57 | 11 (20.4%) | 5.10E−07 | 8.19E−06 | Reactome |
| DNA replication-*Mus musculus* (mouse) | 36 | 9 (25.0%) | 9.04E−07 | 1.30E−05 | KEGG |
| S Phase | 72 | 12 (17.4%) | 9.34E−07 | 1.30E−05 | Reactome |
| p53 signaling pathway-*Mus musculus* (mouse) | 70 | 12 (17.4%) | 9.34E−07 | 1.30E−05 | KEGG |
| Orc1 removal from chromatin | 31 | 8 (28.6%) | 1.22E−06 | 1.57E−05 | Reactome |
| Switching of origins to a post-replicative state | 31 | 8 (28.6%) | 1.22E−06 | 1.57E−05 | Reactome |
| Pathways in cancer-*Mus musculus* (mouse) | 326 | 27 (8.4%) | 1.66E−06 | 2.04E−05 | KEGG |
| ECM-receptor interaction-*Mus musculus* (mouse) | 86 | 13 (15.1%) | 1.73E−06 | 2.06E−05 | KEGG |
| Small cell lung cancer-*Mus musculus* (mouse) | 88 | 13 (14.9%) | 1.98E−06 | 2.27E−05 | KEGG |
| DNA strand elongation | 31 | 8 (25.8%) | 2.87E−06 | 3.18E−05 | Reactome |

TABLE 3-continued

Pathways significantly differed in the 4-NQO + CD1530 group vs. the 4-NQO group

| pathway name | set size | candidates contained | p-value | q-value | pathway source |
|---|---|---|---|---|---|
| Cyclin B2 mediated events | 5 | 4 (80.0%) | 4.12E−06 | 4.41E−05 | Reactome |
| Cyclin A/B1 associated events during G2/M transition | 16 | 6 (37.5%) | 4.69E−06 | 4.86E−05 | Reactome |

Upregulated in the 4-NQO + CD1530 group vs. the 4-NQO group

| pathway name | set size | candidates contained | p-value | q-value | pathway source |
|---|---|---|---|---|---|
| Metabolism | 1039 | 181 (18.6%) | 9.20E−52 | 3.94E−49 | Reactome |
| Drug metabolism-cytochrome P450-*Mus musculus* (mouse) | 87 | 52 (59.8%) | 3.03E−42 | 6.48E−40 | KEGG |
| Metabolism of xenobiotics by cytochrome P450-*Mus musculus* (mouse) | 90 | 50 (55.6%) | 1.93E−38 | 2.75E−36 | KEGG |
| Biological oxidations | 160 | 64 (40.5%) | 3.19E−38 | 3.41E−36 | Reactome |
| Phase 1-Functionalization of compounds | 100 | 51 (51.5%) | 5.43E−37 | 4.65E−35 | Reactome |
| nicotine degradation II | 63 | 41 (65.1%) | 1.17E−35 | 8.37E−34 | MouseCyc |
| Xenobiotics | 39 | 31 (81.6%) | 2.57E−32 | 1.57E−30 | Reactome |
| Retinol metabolism-*Mus musculus* (mouse) | 79 | 42 (53.2%) | 2.47E−31 | 1.32E−29 | KEGG |
| Cytochrome P450-arranged by substrate type | 83 | 42 (55.7%) | 1.88E−30 | 8.95E−29 | Reactome |
| nicotine degradation III | 55 | 35 (63.6%) | 4.68E−30 | 2.00E−28 | MouseCyc |
| bupropion degradation | 39 | 29 (74.4%) | 3.55E−28 | 1.38E−26 | MouseCyc |
| Complement and coagulation cascades-*Mus musculus* (mouse) | 76 | 38 (50.0%) | 3.94E−27 | 1.40E−25 | KEGG |
| Metabolic pathways-*Mus musculus* (mouse) | 1212 | 160 (13.4%) | 1.08E−26 | 3.54E−25 | KEGG |
| Metabolism of lipids and lipoproteins | 265 | 57 (21.8%) | 1.09E−18 | 3.35E−17 | Reactome |
| Linoleic acid metabolism-*Mus musculus* (mouse) | 45 | 24 (53.3%) | 2.09E−18 | 5.96E−17 | KEGG |
| Metabolism of amino acids and derivatives | 127 | 34 (27.4%) | 1.22E−14 | 3.26E−13 | Reactome |
| Bile acid and bile salt metabolism | 38 | 19 (50.0%) | 3.80E−14 | 9.56E−13 | Reactome |
| Formation of Fibrin Clot (Clotting Cascade) | 35 | 18 (52.9%) | 4.92E−14 | 1.17E−12 | Reactome |
| Synthesis of bile acids and bile salts via 7alpha-hydroxycholesterol | 23 | 15 (65.2%) | 9.19E−14 | 2.07E−12 | Reactome |
| Drug metabolism-other enzymes-*Mus musculus* (mouse) | 56 | 22 (39.3%) | 1.82E−13 | 3.89E−12 | KEGG |
| Lipoprotein metabolism | 32 | 16 (51.6%) | 2.19E−12 | 4.46E−11 | Reactome |
| Synthesis of bile acids and bile salts | 27 | 15 (55.6%) | 2.61E−12 | 5.08E−11 | Reactome |
| Bile secretion-*Mus musculus* (mouse) | 71 | 23 (32.4%) | 5.83E−12 | 1.09E−10 | KEGG |
| PPAR signaling pathway-*Mus musculus* (mouse) | 81 | 24 (29.6%) | 1.73E−11 | 3.09E−10 | KEGG |
| Arachidonic acid metabolism-*Mus musculus* (mouse) | 94 | 25 (26.6%) | 8.90E−11 | 1.52E−09 | KEGG |
| Lipid digestion, mobilization, and transport | 50 | 18 (36.7%) | 1.13E−10 | 1.85E−09 | Reactome |
| Steroid hormone biosynthesis-*Mus musculus* (mouse) | 55 | 19 (34.5%) | 1.18E−10 | 1.87E−09 | KEGG |
| Synthesis of bile acids and bile salts via 24-hydroxycholesterol | 18 | 11 (61.1%) | 5.80E−10 | 8.57E−09 | Reactome |
| Chylomicron-mediated lipid transport | 18 | 11 (61.1%) | 5.80E−10 | 8.57E−09 | Reactome |
| Tryptophan metabolism-*Mus musculus* (mouse) | 44 | 16 (36.4%) | 1.48E−09 | 2.11E−08 | KEGG |
| Platelet degranulation | 65 | 19 (29.7%) | 2.22E−09 | 3.07E−08 | Reactome |
| Common Pathway | 13 | 9 (69.2%) | 4.60E−09 | 6.16E−08 | Reactome |
| Response to elevated platelet cytosolic Ca2+ | 71 | 19 (27.1%) | 1.16E−08 | 1.51E−07 | Reactome |
| Miscellaneous substrates | 18 | 10 (55.6%) | 1.31E−08 | 1.65E−07 | Reactome |
| Phenylalanine and tyrosine catabolism | 8 | 7 (87.5%) | 1.80E−08 | 2.20E−07 | Reactome |
| Intrinsic Pathway | 21 | 10 (50.0%) | 4.98E−08 | 5.92E−07 | Reactome |
| Maturity onset diabetes of the young-*Mus musculus* (mouse) | 26 | 11 (42.3%) | 9.14E−08 | 1.03E−06 | KEGG |
| Ascorbate and aldarate metabolism-*Mus musculus* (mouse) | 26 | 11 (42.3%) | 9.14E−08 | 1.03E−06 | KEGG |
| HDL-mediated lipid transport | 18 | 9 (52.9%) | 1.26E−07 | 1.39E−06 | Reactome |
| Complement cascade | 124 | 11 (39.3%) | 2.28E−07 | 2.44E−06 | Reactome |
| Synthesis of bile acids and bile salts via 27-hydroxycholesterol | 14 | 8 (57.1%) | 3.01E−07 | 3.14E−06 | Reactome |
| Peroxisome-*Mus musculus* (mouse) | 79 | 18 (22.8%) | 5.12E−07 | 5.22E−06 | KEGG |
| Biosynthesis of unsaturated fatty acids-*Mus musculus* (mouse) | 25 | 10 (40.0%) | 6.73E−07 | 6.70E−06 | KEGG |
| Transport of gamma-carboxylated protein precursors from the ER to the Golgi apparatus | 8 | 6 (75.0%) | 1.03E−06 | 9.99E−06 | Reactome |
| Pentose and glucuronate interconversions-*Mus musculus* (mouse) | 32 | 11 (34.4%) | 1.10E−06 | 1.03E−05 | KEGG |
| Propanoate metabolism-*Mus musculus* (mouse) | 33 | 11 (34.4%) | 1.10E−06 | 1.03E−05 | KEGG |
| Primary bile acid biosynthesis-*Mus musculus* (mouse) | 16 | 8 (50.0%) | 1.16E−06 | 1.06E−05 | KEGG |
| Glycine, serine and threonine metabolism-*Mus musculus* (mouse) | 39 | 12 (30.8%) | 1.38E−06 | 1.23E−05 | KEGG |
| Serotonergic synapse-*Mus musculus* (mouse) | 140 | 24 (17.3%) | 1.60E−06 | 1.40E−05 | KEGG |
| Removal of aminoterminal propeptides from gamma-carboxylated proteins | 9 | 6 (66.7%) | 2.93E−06 | 2.46E−05 | Reactome |
| Gamma-carboxylation of protein precursors | 9 | 6 (66.7%) | 2.93E−06 | 2.46E−05 | Reactome |
| Fatty acid metabolism-*Mus musculus* (mouse) | 49 | 13 (26.5%) | 3.25E−06 | 2.68E−05 | KEGG |
| Activation of C3 and C5 | 6 | 5 (83.3%) | 3.97E−06 | 3.15E−05 | Reactome |

TABLE 3-continued

Pathways significantly differed in the 4-NQO + CD1530 group vs. the 4-NQO group

| pathway name | set size | candidates contained | p-value | q-value | pathway source |
|---|---|---|---|---|---|
| Terminal pathway of complement | 6 | 5 (83.3%) | 3.97E−06 | 3.15E−05 | Reactome |
| beta-Alanine metabolism-*Mus musculus* (mouse) | 30 | 10 (33.3%) | 4.73E−06 | 3.68E−05 | KEGG |
| Recycling of bile acids and salts | 14 | 7 (50.0%) | 5.64E−06 | 4.31E−05 | Reactome |
| Gamma-carboxylation, transport, and amino-terminal cleavage of proteins | 10 | 6 (60.0%) | 6.95E−06 | 5.22E−05 | Reactome |
| Phase II conjugation | 61 | 14 (23.3%) | 7.10E−06 | 5.24E−05 | Reactome |
| Tyrosine metabolism-*Mus musculus* (mouse) | 39 | 11 (28.2%) | 9.83E−06 | 7.13E−05 | KEGG |

TABLE 4

Pathways significantly differed in the 4-NQO + bexarotene + CD1530 group vs. the 4-NQO group

| pathway name | set size | candidates contained | p-value | q-value | pathway source |
|---|---|---|---|---|---|
| Down-regulated in the 4-NQO + Bexarotene + CD1530 group vs. the 4-NQO group | | | | | |
| Cell Cycle, Mitotic | 277 | 60 (22.4%) | 3.68E−26 | 1.60E−23 | Reactome |
| DNA Replication | 163 | 46 (29.3%) | 1.71E−25 | 3.72E−23 | Reactome |
| Cell Cycle | 314 | 62 (20.4%) | 1.12E−24 | 1.62E−22 | Reactome |
| Mitotic M-M/G1 phases | 141 | 40 (29.6%) | 1.83E−22 | 1.99E−20 | Reactome |
| M Phase | 102 | 27 (27.3%) | 1.66E−14 | 1.44E−12 | Reactome |
| Cytokine-cytokine receptor interaction-*Mus musculus* (mouse) | 245 | 42 (17.1%) | 4.33E−14 | 3.14E−12 | KEGG |
| Mitotic Prometaphase | 98 | 25 (26.3%) | 3.92E−13 | 2.44E−11 | Reactome |
| Cell Cycle Checkpoints | 82 | 20 (26.0%) | 1.21E−10 | 6.59E−09 | Reactome |
| G2/M Checkpoints | 45 | 15 (33.3%) | 5.65E−10 | 2.73E−08 | Reactome |
| Synthesis of DNA | 57 | 16 (29.6%) | 1.08E−09 | 4.70E−08 | Reactome |
| Activation of the pre-replicative complex | 29 | 12 (41.4%) | 1.73E−09 | 6.82E−08 | Reactome |
| Cell cycle-*Mus musculus* (mouse) | 127 | 24 (18.9%) | 2.01E−09 | 7.16E−08 | KEGG |
| Mitotic G1-G1/S phases | 76 | 18 (24.7%) | 2.62E−09 | 7.16E−08 | Reactome |
| DNA replication-*Mus musculus* (mouse) | 36 | 13 (36.1%) | 2.64E−09 | 7.16E−08 | KEGG |
| DNA Replication Pre-Initiation | 39 | 13 (36.1%) | 2.64E−09 | 7.16E−08 | Reactome |
| M/G1 Transition | 39 | 13 (36.1%) | 2.64E−09 | 7.16E−08 | Reactome |
| DNA strand elongation | 31 | 12 (38.7%) | 4.32E−09 | 1.10E−07 | Reactome |
| S Phase | 72 | 17 (24.6%) | 7.40E−09 | 1.79E−07 | Reactome |
| G1/S Transition | 65 | 16 (25.8%) | 1.00E−08 | 2.29E−07 | Reactome |
| Rheumatoid arthritis-*Mus musculus* (mouse) | 83 | 18 (22.2%) | 1.55E−08 | 3.38E−07 | KEGG |
| Removal of licensing factors from origins | 33 | 11 (36.7%) | 3.79E−08 | 7.49E−07 | Reactome |
| Regulation of DNA replication | 33 | 11 (36.7%) | 3.79E−08 | 7.49E−07 | Reactome |
| Activation of ATR in response to replication stress | 38 | 12 (31.6%) | 6.20E−08 | 1.17E−06 | Reactome |
| Unwinding of DNA | 11 | 7 (63.6%) | 1.09E−07 | 1.97E−06 | Reactome |
| Hematopoietic cell lineage-*Mus musculus* (mouse) | 84 | 17 (20.7%) | 1.17E−07 | 2.03E−06 | KEGG |
| Assembly of the pre-replicative complex | 25 | 9 (40.9%) | 2.25E−07 | 3.77E−06 | Reactome |
| Orc1 removal from chromatin | 31 | 9 (32.1%) | 2.45E−06 | 3.81E−05 | Reactome |
| Switching of origins to a post-replicative state | 31 | 9 (32.1%) | 2.45E−06 | 3.81E−05 | Reactome |
| Cyclin A/B1 associated events during G2/M transition | 16 | 7 (43.8%) | 3.08E−06 | 4.62E−05 | Reactome |
| Jak-STAT signaling pathway-*Mus musculus* (mouse) | 153 | 21 (13.7%) | 5.34E−06 | 7.74E−05 | KEGG |
| APC/C-mediated degradation of cell cycle proteins | 44 | 10 (25.0%) | 8.49E−06 | 0.000115 | Reactome |
| Regulation of mitotic cell cycle | 44 | 10 (25.0%) | 8.49E−06 | 0.000115 | Reactome |
| Upregulated in the 4-NQO + Bexarotene + CD1530 group vs. the 4-NQO group | | | | | |
| Fatty acid, triacylglycerol, and ketone body metabolism | 66 | 12 (18.8%) | 3.35E−07 | 0.000101 | Reactome |
| Dilated cardiomyopathy-*Mus musculus* (mouse) | 91 | 13 (14.6%) | 2.15E−06 | 0.000248 | KEGG |
| Tight junction-*Mus musculus* (mouse) | 137 | 16 (11.8%) | 2.79E−06 | 0.000248 | KEGG |
| Propanoate metabolism-*Mus musculus* (mouse) | 33 | 8 (25.0%) | 3.31E−06 | 0.000248 | KEGG |

What is claimed is:

1. A method for treating an oral cancer in a subject, the method comprising: administering to said subject a Retinoid X Receptor (RXR) agonist in combination with a Retinoic Acid Receptor (RAR) agonist, wherein said RXR agonist is bexarotene and said RAR agonist is CD1530, thereby treating said cancer in said subject.

2. The method of claim 1, wherein said cancer is oral squamous cell carcinoma.

3. The method of claim 1, wherein said administration of said RXR agonist in combination with said RAR agonist reduces the number of cancer stem cells in oral cavity.

4. The method of claim 1, wherein said administration is an oral administration.

5. The method of claim 4, wherein said administration is by oral medication.

6. The method of claim 1, wherein said administration is intravenous or subcutaneous administration.

7. The method of claim 1, wherein said administration is a coadministration of said RXR agonist and said RAR agonist.

8. The method of claim 1, wherein said administration comprises an independent administration of RXR agonist and said RAR agonist.

9. The method of claim 1, wherein said cancer is locally advanced.

10. The method of claim 1, wherein said cancer is caused by tobacco, cigar smoking, alcohol, virus, carcinogen, irradiation, or a combination thereof.

* * * * *